US008119395B1

(12) United States Patent
Weiner et al.

(10) Patent No.: US 8,119,395 B1

(45) Date of Patent: Feb. 21, 2012

(54) VACCINES, IMMUNOTHERAPEUTICS AND METHODS FOR USING THE SAME

(75) Inventors: David B. Weiner, Merion Station, PA (US); Jong J. Kim, North Wales, PA (US); Jeong-Im Sin, Seoul (KR)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/622,452

(22) PCT Filed: Feb. 26, 1999

(86) PCT No.: PCT/US99/04332

§ 371 (c)(1), (2), (4) Date: Oct. 31, 2000

(87) PCT Pub. No.: WO99/43839

PCT Pub. Date: Sep. 2, 1999

Related U.S. Application Data

(60) Provisional application No. 60/076,207, filed on Feb. 27, 1998.

(51) Int. Cl.
*C12N 15/85* (2006.01)
*A61K 48/00* (2006.01)
*C12N 15/33* (2006.01)

(52) U.S. Cl. .................................. 435/320.1; 514/44 R

(58) Field of Classification Search ............... 435/320.1, 435/455, 325; 514/44 R, 44

See application file for complete search history.

(56) References Cited

U.S. PATENT DOCUMENTS

| | | | | |
|---|---|---|---|---|
| 4,722,848 A | | 2/1988 | Paoletti et al. | 424/89 |
| 4,945,050 A | | 7/1990 | Sanford et al. | 435/172.1 |
| 5,017,487 A | | 5/1991 | Stunnenberg et al. | 435/172.3 |
| 5,036,006 A | | 7/1991 | Sanford et al. | 435/170.1 |
| 5,077,044 A | | 12/1991 | Stocker | 424/92 |
| 5,110,587 A | | 5/1992 | Paoletti et al. | 424/89 |
| 5,112,749 A | | 5/1992 | Brey, III et al. | 435/172.3 |
| 5,174,993 A | | 12/1992 | Paoletti | 424/89 |
| 5,223,424 A | | 6/1993 | Cochran et al. | 435/236 |
| 5,225,336 A | | 7/1993 | Paoletti | 435/69.1 |
| 5,240,703 A | | 8/1993 | Cochran | 424/89 |
| 5,242,829 A | | 9/1993 | Panicali et al. | 435/320.1 |
| 5,294,441 A | | 3/1994 | Curtiss, III | 424/93 A |
| 5,294,548 A | | 3/1994 | McLinden et al. | 435/235.1 |
| 5,310,668 A | | 5/1994 | Ellis et al. | 435/172.3 |
| 5,387,744 A | | 2/1995 | Curtiss, III et al. | 424/235.1 |
| 5,389,368 A | | 2/1995 | Gurtiss, III | 424/93.2 |
| 5,424,065 A | | 6/1995 | Curtiss, III et al. | 424/88 |
| 5,451,499 A | | 9/1995 | Cochran | 435/5 |
| 5,453,364 A | | 9/1995 | Paoletti | 435/69.3 |
| 5,462,734 A | | 10/1995 | Letchworth, III et al. | 424/229.1 |
| 5,470,734 A | | 11/1995 | Sondermeijer et al. | 424/229.1 |
| 5,482,713 A | | 1/1996 | Paoletti | 424/199.1 |
| 5,494,807 A | * | 2/1996 | Paoletti et al. | 435/69.3 |
| 5,593,972 A | | 1/1997 | Weiner et al. | 514/44 |
| 5,693,622 A | * | 12/1997 | Wolff et al. | 514/44 |
| 5,739,118 A | | 4/1998 | Carrano et al. | 514/44 |
| 5,830,876 A | | 11/1998 | Weiner et al. | 514/44 |
| 5,837,533 A | | 11/1998 | Boutin | 435/320.1 |
| 5,916,879 A | * | 6/1999 | Webster | 514/44 R |
| 5,962,428 A | | 10/1999 | Carrano et al. | |
| 5,990,301 A | * | 11/1999 | Colpan et al. | 536/25.4 |
| 6,197,755 B1 | | 3/2001 | Carrano et al. | |
| 6,204,250 B1 | * | 3/2001 | Bot et al. | 514/44 R |
| 6,417,328 B2 | | 7/2002 | Alnemri | |

FOREIGN PATENT DOCUMENTS

| | | | |
|---|---|---|---|
| WO | WO 95/24485 | | 9/1995 |
| WO | WO 96/11279 | | 4/1996 |
| WO | WO 96/26285 | | 8/1996 |
| WO | WO 96/36366 | * | 11/1996 |
| WO | WO 96/40267 | | 12/1996 |
| WO | WO 99/43839 | | 9/1999 |

OTHER PUBLICATIONS

MacFarlane et al. (1997) J. Biol. Chem., vol. 272 (41) 25417-25420.*
Sheridan et al. (1997) Science, vol. 277, 818-821.*
Abbas et al. (1996) Nature, vol. 383, 787-793.*
Golding et al. (1994) Am. J. Trop. Med. Hyg., vol. 50 (4), 33-40.*
Monteil et al. (1996) Veterinary Research, vol. 27 (4-5), 443-452.*
Yasutomi et al. (1995) J. Virol., vol. 69 (4), 2279-2284.*
Ertl et al. (1996), Viral Immunology, vol. 9 (1), 1-9.*
Erdile et al. (2000) Cancer Immunology Immunotherapy 49 (8): 410-416.*
Klein et al. (2000) Clinical Therapeutics, vol. 22 (3), 295-314.*
Fox (1994) Bio/Technology, 12, 128.*
Prayaga et al. (1997) Vaccine, vol. 15 (12/13), 1349-1352.*
Mendoza, R.B., et al., "Cutting edge: Immunostimulatory effects of a plasmid expressing CD40 ligand (CD154) on gene immunization," *Am. Assoc. Immunologists*, 1997, 5777-5781.
Uzendoski, K., et al., "Construction and characterization of a recombinant vaccinia virus expressing murine intercellular adhesion molecule-1: induction and potentiation of antitumor responses," *Human Gene Therapy*, 1997, 8, 851-860.
Alnemri, E.S., et al., "Cloning and expression of four novel isoforms of human interleukin-1 β converting enzyme with different appoptotic activities," *J. Biol. Chem.*, 1995, 270(9), 4312-4317.
Arai, N., et al., "Complete nucleotide sequence of the chromosomal gene for human IL-4 and its expression," *J. Immunol.*, 1989, 142, 274-282.
Azuma, M., et al., "B70 antigen is a second ligand for CTLA-4 and CD28," *Nature*, 1993, 366, 76-79.
Bodmer, J., et al., TRAMP, a novel apoptosis-mediating receptor with sequence homology to tumor necrosis factor receptor 1 and Fas(Apo-1/CD95), *Immunity*, 1997, 61(1), 79-88.
Boyer, J.D., et al., "Protection of chimpanzees from high-dose heterologous HIV-1 challenge by DNA vaccination," *Nature Med.*, 1997, 3, 526-532.

(Continued)

*Primary Examiner* — Anne Marie S Wehbe

(74) *Attorney, Agent, or Firm* — Pepper Hamilton, LLP

(57) ABSTRACT

Improved vaccines which include a nucleotide sequence that encodes immunomodulating protein operably linked to regulatory elements are disclosed. The improved vaccines include DNA vaccines, recombinant vaccines for delivering foreign antigen and live attenuated vaccines. Methods of immunizing individuals are disclosed. Compositions for and methods of treating individuals with autoimmune diseases are disclosed.

40 Claims, 3 Drawing Sheets

OTHER PUBLICATIONS

Chaudhary, V.K., et al., "A rapid method of cloning functional variable-region antibody genes in *Escherichia coli* as single-chain immunotoxins," *Proc. Natl. Acad. Sci. USA*, 1990, 87, 1066-1070.
Chinnaiyan, A.M., et al., "Signal transduction by DR3, a death domain-containing receptor related to TNFR-1 and CD95," *Science*, 1996, 274, 990-992.
Corbi, A.L., et al., "The uman leukocyte adhesion glycoprotein mac-1 (complement receptor type 3, CD11b) α subunit," *J. Biol. Chem.*, 1988, 263(25), 12403-12411.
Corbi, A.L., et al., "cDNA cloning and complete primary structure of the α subunit of a leukocyte adhesion glycoprotein, p150,95," *EMBO J.*, 1987, 6(13), 4023-4028.
Degli-Esposti, M.A., et al., "Air, a novel member of the TNF receptor family, is a strong inducer of apoptosis," *Genbank*, Accession No. U78029, GI: 1778763, 1977, 1 page.
Elices, M.J., "VCAM-1 on activated endothelium interacts with the leukocyte integrin VLA-4 at a site distinct from the VLA-4/fibronectin binding site," *Cell*, 1990, 60, 577-584.
Gauchat, J.F.M., "Human CD40-ligand: molecular cloning, cellular distribution and regulation of expression by factors controlling IgE production," *FEBS Lett.*, 1993, 315(3), 259-266.
Goodwin, R.G., et al., "Human interleukin 7: molecular cloning and growth factor activity on human and murine B-lineage cells," *Proc. Natl. Acad. Sci. U.S.A.*, 1989, 86, 302-306.
Gray, P.W., et al., "Cloning of human tumor necrosis factor (TNF) receptor cDNA and expression of recombinant soluble TNF-binding protein," *Proc. Natl. Acad. Sci. U.S.A.*, 1990, 87, 7380-7384.
Han, H.J., et al., "Dinucleotide repeat polymorphism in the 3' noncoding region of the FLTI gene,"Human Molecular *Genet.*, 1993, 2(12), p. 2204.
Himmler, A., et al., "Molecular cloning and expression of human and rat tumor necrosis factor receptor chain (p60) and its soluble derivative, tumor necrosis factor-binding protein," *DNA Cell Biol.*, 1990, 9, 705-715.
Howell, M.D., et al., "Limited T-cell receptor β-chain heterogeneity among interleukin 2 receptor-positive synovial T cells suggests a role for superantigen in rheumatoid arthritis," *Proc. Natl. Acad. Sci. USA*, 1991, 88,10921-10925.
Itoh, N., et al., "The polypeptide encoded by the cDNA for human cell surface antigen fas can mediate apoptosis," *Cell*, 1991, 66, 233-243.
Johnson, D., et al., "Expression and structure of the human NGF receptor," *Cell*, 1986, 47(4), 545-554.
Johnston, G.I., et al., "Cloning of GMP-140, a granule membrane protein of platelets and endothelium: sequence similarity to proteins involved in cell adhesion and inflammation," *Cell*, 1989, 56, 1033-1044.
Kim, J.J., et al., "DNA gene vaccination for HIV," *Springer Sem Immunopathol*, 1997, 19, 174-194.
Kim, J.J., et al., "Engineering of in vivo immune responses to DNA immunization via codelivery of costimulatory molecule genes," *Nature Biot.*, 1997, 15, 641-646.
Kim, J.J., et al., "CD8 positive T cells influence antigen-specific immune responses through the expression of chemokines," *J. Clin. Invest.*, 1998, 102, 1112-1124.
Kim, J.J., et al., "Modulation of amplitude and direction of in vivo immune responses by co-administration of cytokine gene expression cassettes with DNA immunogens," *Eur. J. Immunol.*, 1998, 28, 1089-1103.
Kim, J.J., et al., "In vivo engineering of a cellular immune response by coadministration of IL-12 expression vector with a DNA immunogen," *J. Immunol.*, 1997, 158, 816-826.
Kitson, J., et al., "A death-domain-containing receptor that mediates apoptosis," *Nature*, 1996, 384, 372-375.
Kretschmer, P.J., et al., "Cloning, characterization and development regulation of two members of a novel human gene family of neurite outgrowth-promoting proteins," *Growth Factors*, 1991, 5, 99-114.
Larson, R.S., et al., "Primary structure of the leukocyte function-associated molecule-1 α subunit: an integrin with an embedded domain defining a protein superfamily," *J. Cell Biol.*, 1989, 108, 703-712.
Lee, F., et al., "Isolation of cDNA for a human granulocyte-macrophage colony-stimulating factor by functional expression in mammalian cells," *Proc. Natl. Acad. Sci. USA*, 1985, 82, 4360-4364.
Leung, D.W., et al., "Vascular endothelial growth factor is a secreted angiogenic mitogen," *Science*, 1989, 246, 1306-1309.
Leung, E., et al., "Genomic organization, chromosomal mapping, and analysis of the 5' promoter region of the human MAdCAM-lgene," *Immunogenetics*, 1997, 46, 111-119.
Loetscher, H., et al., "Molecular cloning and expression of the human 55 kd tumor necrosis factor receptor," *Cell*, 1990, 61, 351-359.
Mandriota, S.J., et al., "Transforming growth factor β1 down-regulates vascular endothelial growth factor receptor 1/*flk*-1 expression in vascular endothelial cells," *J. Biol. Chem.*, 1996, 271(19), 11500-11505.
Marsters, S.A., et al., "Apo-3, a new member of the tumor necrosis factor receptor family, contains a death domain and activates apoptosis and NF-kB," *Curr. Biol.*, 1996, 6(2), 1669-1676.
Nagata, S., et al., "The chromosomal gene structure and two mRNAs for human granulocyte colony-stimulating factor," *EMBO J.*, 1986, 5(3), 575-581.
Newman, P.J., et al., "PECAM-1 (CD31) cloning and relation to adhesion molecules of the immunoglobulin gene superfamily," *Science*, 1990, 247, 1219-1222.
Nophar, Y., et al., "Soluble forms of tumor necrosis factor receptors (TNF-Rs). The cDNA for the type 1 TNF-R, cloned using amino acid sequence data of its soluble form, encodes both the cell surface and a soluble form of the receptor," *EMBO J.*, 1990, 9(10), 3269-3278.
Oehm, A., et al., "Purification and molecular cloning of the APO-1 cell surface antigen, a member of the tumor necrosis factor/nerve growth factor receptor superfamily," *J. Biol. Chem.*, 1992, 267(15), 10709-10715.
Oksenbert, J.R., et al., "Limited heterogeneity of rearranged T-cell receptor Vα transcripts in brains of multiple sclerosis patients," *Nature*, 1990, 345, 344-346.
Osborn, L., et al., "Direct expression cloning of vascular cell adhesion molecule 1, a cytokine-induced endothelial protein that binds to lymphocytes," *Cell*, 1989, 59, 1203-1211.
Pachuk, C.J., et al., Current topics in microbiology and immunology, *Curr. Topics Microbiol. Immunol.*, 1998, 226, 79-89.
Paliard, X., et al., "Evidence for the effects of a superantigen in rheumatoid arthritis," *Science*, 1991, 253, 325-329.
Pan, et al., "The receptor for the cytotoxic ligand trail," *Science*, 1997, 276(5309), 111-113.
Pan, et al., "Identification and functional characterization of DR6, a novel death domain-containing TNF receptor," *Genbank*, 1998, Accession No. AF068868, 2 pages.
Screaton, G.R., et al., "TRICK2, a new alternatively spliced receptor that transduces the cytotoxic signal from TRAIL," *Curr. Biol.*, 1997, 7(9), 693-696.
Screaton, G.R., et al., "LARD: a new lymphoid-specific death domain containing receptor regulated by alternative pre-mRNA splicing," *Proc. Natl. Acad. Sci. USA*, 1997, 94, 4615-4619.
Sheridan, J.P., et al., "Control of TRAIL-induced apoptosis by a family of signaling and decoy recetors," *Science*, 1997, 277, 818-821.
Shibuya, M., et al., "Nucleotide sequence and expression of a novel human receptor-type tyrosine kinase gene (*flt*) closely related to the *fms* family," *Oncongene*, 1990, 5, 519-524.
Shyjan, A.M., et al., "human mucosal addressin cell adhesion molecule-1 (MadCAM-1) demonstrates structural and functional similarities to the $\alpha_4\beta_7$-integrin binding domains of murine MadCAM-1, but extreme divergence of mucin-like sequences," *J. Immunol.*, 1996, 156, 2851-2857.
Simmons, D.L., et al., "Molecular cloning of a cDNA encoding CD34, a sialomucin of human hematopoietic stem cells," *J. Immunol.*, 1992, 148(1), 267-271.
Springer, T.A., et al., "The lymphocyte function-associated LFA-1, CD2, and LFA-3 molecules: cell adhesion receptors of the immune system," *Ann. Rev. Immunol.*, 1987, 5, 223-252.
Staunton, D.E., et al., "Functional cloning of ICAM-2, a cell adhesion ligand for LFA-1 homologous to ICAM-1," *Nature*, 1989, 339, 61-64.
Staunton, D.E., et al., "Primary structure of ICAM-1 demonstrates interaction between members of the immunoglobulin and integrin supergene families," *Cell*, 1988, 52, 925-933.

Takada, Y., et al., "The primary structure of the VLA-2/colagen receptor $\alpha^2$ subunit (platelet GPIa): homology to other integrins and the presence of a possible collagen-binding domain," *J. Cell Biol.*, 1989, 109, 397-407.

Takahashi, M., et al., "Amino-terminal region of human macrophage colony-stimulating factor (MCSF) is sufficient for its in vitor biological activity: molecular cloning and expression of carboxyl-terminal deletion mutants of human M-CSF," *Biochem. Biophys. Res. Commun.*, 1989, 161(2), 892-901.

Wallner, B.P., et al., "Primary structure of lymphocyte function-associated antigen 3 (LAF-3). The ligand of the T lymphocyte CD2 glycoprotein," *J. Exper. Med.*, 1987, 166, 923-932.

Williams, W.V., et al., "Restricted heterogeneity of T cell receptor transcripts in rheumatoid synovium," *J. Clin. Invest.*, 1992, 90, 326-333.

Wong, G.G., et al., "Human CSF-1: molecular cloning and expression of 4-kd cDNA encoding the human urinary protein," *Science*, 1987, 235, 1504-1508.

Wong, G.G., et al., "Human GM-CSF: Molecuar cloning of the complementary DNA and purification of the natural and recombinant proteins," *Science*, 1985, 228, 810-815.

Wu, G.S., et al., "Killer/DR5 is a DNA damage-inducible p53-regulated death receptor gene," *Nature Genetics*, 1997, 17, 141-143.

Wucherpfennig, K.W., et al., "Shared human T cell receptor $V_\beta$ usage to immunodominant regions of myelin basic protein," *Science*, 1990, 248, 1016-1019.

Yokota, T., et al., "Isolation and characterization of a human interleukin cDNA clone, homologous to mouse B-cell stimulatory factor 1, that expresses B-cell-and T-cell-stimulating activities," *Proc. Natl. Acad. Sci. USA*, 1986, 83, 5894-5898.

Caamaño, et al., "Nuclear Factor (NF)-κb2 (p100/p52) is Required for Normal Splenic Microarchitecture and B Cell-mediated Immune Responses," *The Journal of Experimental Medicine*, (1998) 187(2):185-196.

Chattergoon, et al., "Targeted antigen delivery to antigen-presenting cells including dendritic cells by engineered Fas-mediated apoptosis," *Nature Biotechnology* (2000) 18:974-979.

Chattergoon, et al., "DR5 triggered apoptosis functions as a vaccine adjuvant by inducing caspase-8 dependent dendritic cell maturation," (27 pp.).

Chaudhary, et al., "Death Receptor 5, a New Member of the TNFR Family, and DR4 Induce FADD-Dependent apoptosis and Activate the NF-κB Pathway," *Immunity* (1997) 7:821-830.

Chow et al., "Development of Th1 and Th2 populations and the nature of immune responses to hepatitis B virus DNA vaccines can be modulated by codelivery of various cytokine genes," *J Immunol* (1988) 140(4):1320-1329.

Denich, et al., "Expression of the Murine Interleukin-4 Gene in an Attenuated aroA Strain of *Salmonella typhimurium*: Persistence and Immune Response in BALB/c Mice and Susceptibility to Macrophase Killing," *Infection and Immunity*, (1993) 61(11):4818-4827.

Geissler et al., "Enhancement of cellular and humoral immune responses to hepatitis C virus core protein using DNA-based vaccines augmented with cytokine- expressing plasmids," *J Immunol* (1997) 158(3):1231-7.

Iwasaki et al., "Enhanced CTL responses mediated by plasmid DNA immunogens encoding costimulatory molecules and cytokines," *J Immunol* (1997) 158(10):4591-4601.

Ramshaw et al., "Expression of cytokines by recombinant vaccinia viruses: a model for studying cytokines in virus infections in vivo," *Immunol Rev* (1992) 127:157-178.

Sha, "Regulation of Immune Responses by NF-κB/Rel Transcription Factors," *J Exp Med* (1998) 187(2):143-146.

Schneider, et al., "TRAIL Receptors 1 (DR4) and 2 (DR5) Signal FADD-Dependent Apoptosis and Activate NF-κB," *Immunity* (1997) 7:831-836.

Tsuji et al., "HIV-1-specific cell-mediated immunity is enhanced by co-inoculation of TCA3 expression plasmid with DNA vaccine," *Immunology* (1997) 90:1-6.

Xiang et al., "Manipulation of the immune response to a plasmid-encoded viral antigen by coinoculation with plasmids expressing cytokines," *Immunity* (1995) 2(2):129-135.

Goya, Inigo et al., "Identification of CCR8 as the Specific Receptor for the Human β-Chemokine I-309: Cloning and Molecular Characterization of Murine CCR8 as the Receptor for TCA-$3_1$", J. Immun., 1998, 160: 1975-1981.

Kuna, P. et al., "Characterization of the human basophil response to cytokines, growth factors, and histamine releasing factors of the intercrine/chemokine family", *J. Immunol.* Mar. 1, 1993;150(5): 1932-43.

Lee, Tiffany et al., "Identification of CCR8: A Human Monocyte and Thymus Receptor for the CC Chemokine I-309", *J. Exp. Med.* 186(1), Jul. 1997, 165-170.

Paolini, J.F. et al., "The chemokines IL-8, monocyte chemoattractant protein-1, and 1-309 are monomers at physiologically relevant concentrations", *J. Immunol.* Sep. 15, 1994; 153(6): 2704-17.

Struber Roos, Regula et al., "Identification of CCR8, the Receptor for the Human CC Chemokine I-309", *Am. Soc. Biochem. & Mol. Biol.* 272(28) Jul. 1997, 17251-17254.

Van Snick, J. et al., "I-309/T cell activation gene-3 chemokine protects murine T cell lymphomas against dexamethoasone-induced apoptosis", *J. Immunol.* Sep. 15, 1996; 157(6):2570-6.

Misfeldt "Microbial 'Superantigens,'" *Infection and Immunity* (1990) 58(8):2409-2413.

Hodtsev, A.S. et al., "Mycoplasma Superantigen is a CDR3-dependent Ligand for the T Cell Antigen Receptor", J. Exp. Med., 187(3): 1996, pp. 319-327.

Mendoza, Robert B. et al., "Cutting Edge: Immunostimulatory Effects of a Plasmid Expressing CD40 Ligand (CD154) on Gene Immunization", The Journal of Immunology, 1997, 159:5777-5781.

Pasquini, S. et al., "Cytokines and costimulatory molecules as genetic adjuvants", Immunology and Cell Biology, 1997, 75:397-401.

Tsuji, T. et al., "Immunomodulatory of a plasmid expressing B7-2 on human immunodeficiency virus-1 specific cell-mediated immunity induced by a plasmid encoding the viral antigen", European Journal of Immunology, 1997, 27:782-787.

* cited by examiner

Mutant IGIF with the first amino acid mutated to Met can potentially bypass Capsase-1 processing hence be more potent

SEQUENCE LISTING

```
<160> NUMBER OF SEQ ID NOS: 1

<210> SEQ ID NO 1
<211> LENGTH: 15
<212> TYPE: PRT
<213> ORGANISM: Human immunodeficiency virus

<400> SEQUENCE: 1

Arg Ile His Ile Gly Pro Gly Arg Ala Phe Tyr Thr Thr Lys Asn
1               5                   10                  15
```

VACCINES, IMMUNOTHERAPEUTICS AND METHODS FOR USING THE SAME

CROSS-REFERENCE TO RELATED APPLICATIONS

This application claims priority to U.S. Provisional Application 60/076,207 filed Feb. 27, 1998 and entitled "Improved Vaccines", which is incorporated herein by reference.

FIELD OF THE INVENTION

The present invention relates to improved vaccines, improved methods for prophylactically and/or therapeutically immunizing individuals against immunogens, and to improved immunotherapeutic compositions and improved immunotherapy methods.

BACKGROUND OF THE INVENTION

Immunotherapy refers to modulating a persons immune responses to impart a desirable therapeutic effect. Immunotherapeuties refer to those compositions which, when administered to an individual, modulate the individual's immune system to decrease symptoms and causes of symptoms brought on by undesirable immune responses or to alleviate symptoms or eliminate/reduce causes of symptoms by increasing desirable immune responses. In some cases, immunotherapy is part of a vaccination protocol in which the individual is administered a vaccine that results in the individual being exposed to an immunogen. In such cases, the immunotherapeutic increases the immune, response and/or selectively enhance a portion of the immune response which is desirable to treat or prevent the particular condition, infection or disease. In some cases, immunotherapeutics are delivered free of immunogens. In such cases, the immunotherapeutics are provided to modulate the immune system by either decreasing or suppressing immune responses, enhancing or increasing immune response, decreasing or suppressing a portion of immune system, enhancing or increasing a portion of the immune system or decreasing or suppressing immune response, enhancing or increasing immune responses. In some cases, immunotherapeutics include antibodies which when administered in vivo, bind to proteins involved in modulating immune responses. The interaction between antibodies and such proteins results in the alteration of immune responses. If the protein is involved in autoimmune disease, the antibodies can inhibit its activity in that role and reduce or eliminate the symptoms or disease.

Vaccines are useful to immunize individuals against target antigens such as allergens, pathogen antigens or antigens associated with cells involved in human diseases. Antigens associated with cells involved in human diseases include cancer-associated tumor antigens and antigens associated with cells involved in autoimmune diseases.

In designing such vaccines, it has been recognized that vaccines which produce the target antigen in the cell of the vaccinated individual are effective in inducing the cellular arm of the immune system. Specifically, live attenuated vaccines, recombinant vaccines which use avirulent vectors and DNA vaccines all lead to the production of antigens in the cell of the vaccinated individual which results induction of the cellular arm of the immune system. On the other hand, subunit vaccines which comprise only proteins and killed or inactivated vaccines, which do induce a humoral response, do not induce good cellular immune responses.

A cellular immune response is often necessary to provide protection against pathogen infection and to provide effective immune-mediated therapy for treatment of pathogen infection, cancer or autoimmune diseases. Accordingly, vaccines which produce the target antigen in the cell of the vaccinated individual such as live attenuated vaccines, recombinant vaccines which use avirulent vectors and DNA vaccines are preferred.

While such vaccines are often effective to immunize individuals prophylactically or therapeutically against pathogen infection or human diseases, there is a need for improved vaccines. There is a need for compositions and methods which produce an enhanced immune response.

SUMMARY OF THE INVENTION

The present invention related compositions which comprise immunomodulating proteins or nucleic acid molecules that encode the same, which enhance and/or modulate the immune response, as well as methods of using such proteins and nucleic acid molecules. The delivery of immunomodulating proteins is useful for immunotherapy as well as for enhancing or otherwise tailoring immune responses in conjunction with vaccine delivery. An immunomodulating proteins may be: a chemokine including MCP-1, MIP-1α, MIP-1β, IL-δ and RANTES; an adhesion molecule including a selectin such as L-selectin, P-selectin and E-selectin, a mucin-like molecule such as CD34, GlyCAM-1, and Mad-CAM-1, a member of the integrin family such as LFA-1, VLA-1, Mac-1 and p150.95, a member of the immunoglobulin superfamily such as PECAM, ICAMs e.g. ICAM-1, ICAM-2 and ICAM-3, CD2 and LFA-3; cytokines including M-CSF, G-CSF, GSF, IL-4, mutant forms of IL-18; co-stimulatory molecules such as CD40 and CD40L; growth factors including vascular growth factor, IL-7, nerve growth factor and vascular endothelial growth factor; receptor molecules including Fas, TNF receptor, Flt, Apo-1, p55, WSL-1, DR3, TRAMP, Apo-3, AIR, LARD, NGRF, DR4, DR6, KILLER, TRAIL-R2, TRICK2, DR6; others include Caspase (ICE).

The present invention relates to a plasmid which comprises a nucleotide sequence that encodes an immunomodulating protein operably linked to regulatory elements necessary for expression in eukaryotic cells and a nucleotide sequence that encodes an immunogen operably linked to regulatory elements necessary for expression in eukaryotic cells. The immunogen is preferably a pathogen antigen, a cancer-associated antigen or an antigen linked to cells associated with autoimmune diseases.

The present invention relates to a method of inducing an immune response in an individual against an immunogen comprising the step of administering to an individual, a plasmid which comprises a nucleotide sequence that encodes an immunomodulating protein operably linked to regulatory elements necessary for expression in cells of the individual, and a nucleotide sequence that encodes an immunogen operably linked to regulatory elements necessary for expression in cells of the individual.

The present invention relates to a method of immunizing an individual against a pathogen, cancer or an autoimmune disease comprising the step of administering to an individual, a plasmid which comprises a nucleotide sequence that encodes an immunomodulating protein operably linked to regulatory elements necessary for expression in cells of the individual, and a nucleotide sequence that encodes an immunogen operably linked to regulatory elements necessary for expression in cells of the individual, wherein the immunogen is a pathogen antigen, a cancer-associated antigen or an antigen linked to cells associated with autoimmune diseases.

The present invention relates to a composition which comprises a first plasmid which comprises a nucleotide sequence that encodes an immunomodulating protein operably linked to regulatory elements necessary for expression in eukaryotic cells and a second plasmid which comprises a nucleotide sequence that encodes an immunogen operably linked to regulatory elements necessary for expression in eukaryotic cells. In some preferred embodiments, the immunogen is a pathogen antigen, a cancer-associated antigen or an antigen linked to cells associated with autoimmune diseases.

The present invention relates to a method of immunizing an individual against a pathogen, cancer or an autoimmune disease comprising the step of administering to an individual, a composition which comprises a first plasmid which comprises a nucleotide sequence that encodes an immunomodulating protein operably linked to regulatory elements necessary for expression in cells of the individual, and a second plasmid which comprises a nucleotide sequence that encodes an immunogen operably linked to regulatory elements necessary for expression in cells of the individual, wherein the immunogen is a pathogen antigen, a cancer-associated antigen or an antigen linked to cells associated with autoimmune diseases.

The present invention relates to a method of inducing an immune response against an immunogen comprising the step of administering to an individual, a composition which comprises a first plasmid which comprises a nucleotide sequence that encodes an immunomodulating protein operably linked to regulatory elements necessary for expression in cells of the individual, and a second plasmid which comprises a nucleotide sequence that encodes an immunogen operably linked to regulatory elements necessary for expression in cells of the individual.

The present invention relates to an improved recombinant vaccine vector which comprises a nucleotide sequence that encodes an immunomodulating protein operably linked to regulatory elements necessary for expression in eukaryotic cells and a nucleotide sequence that encodes a target antigen operably linked to regulatory elements necessary for expression in eukaryotic cells. In preferred embodiments, the target antigen is a pathogen antigen, a cancer-associated antigen or an antigen linked to cells associated with autoimmune diseases.

The present invention relates to a method of immunizing an individual against a pathogen, cancer or an autoimmune disease comprising the step of administering to an individual, a recombinant vaccine vector which comprises a nucleotide sequence that encodes an immunomodulating protein operably linked to regulatory elements necessary for expression in cells of the individual, and a nucleotide sequence that encodes a target antigen operably linked to regulatory elements necessary for expression in cells of the individual, wherein the target antigen is a pathogen antigen, a cancer-associated antigen or an antigen linked to cells associated with autoimmune diseases.

The present invention relates to a method of inducing an immune response against and target antigen comprising the step of administering to an individual, a recombinant vaccine vector which comprises a nucleotide sequence that encodes an immunomodulating protein operably linked to regulatory elements necessary for expression in cells of the individual, and a nucleotide sequence that encodes a target antigen operably linked to regulatory elements necessary for expression in cells of the individual.

The present invention relates to an improved live, attenuated vaccine which comprises a nucleotide sequence that encodes an immunomodulating protein operably linked to regulatory elements necessary for expression in eukaryotic cells.

The present invention relates to a method of immunizing an individual against a pathogen, cancer or an autoimmune disease comprising the step of administering to an individual, an attenuated vaccine which comprises a nucleotide sequence that encodes an immunomodulating protein operably linked to regulatory elements necessary for expression in cells of the individual.

The present invention relates to a method of inducing an immune response in an individual against an immunogen comprising the step of administering to an individual, an attenuated vaccine which comprises a nucleotide sequence that encodes an immunomodulating protein operably linked to regulatory elements necessary for expression in cells of the individual.

The present invention relates to compositions and methods for modulating an individual's immune system. The methods of the invention comprise delivering an immunomodulating protein to an individual, either by administration of protein or administration of a nucleotide sequence that encodes an immunomodulating protein as part of an expression vector or other vehicle capable of delivering a nucleotide sequence to an individual in expressible form.

The present invention relates to compositions and methods for treating individuals who have autoimmune diseases. The methods of the invention comprise administering to such individuals, a composition comprising antibodies that specifically bind to chemokines including MCP-1, MIP-1$\alpha$, MIP-1$\beta$, IL-8 and RANTES.

DETAILED DESCRIPTION OF PREFERRED EMBODIMENTS

Figure 1A:
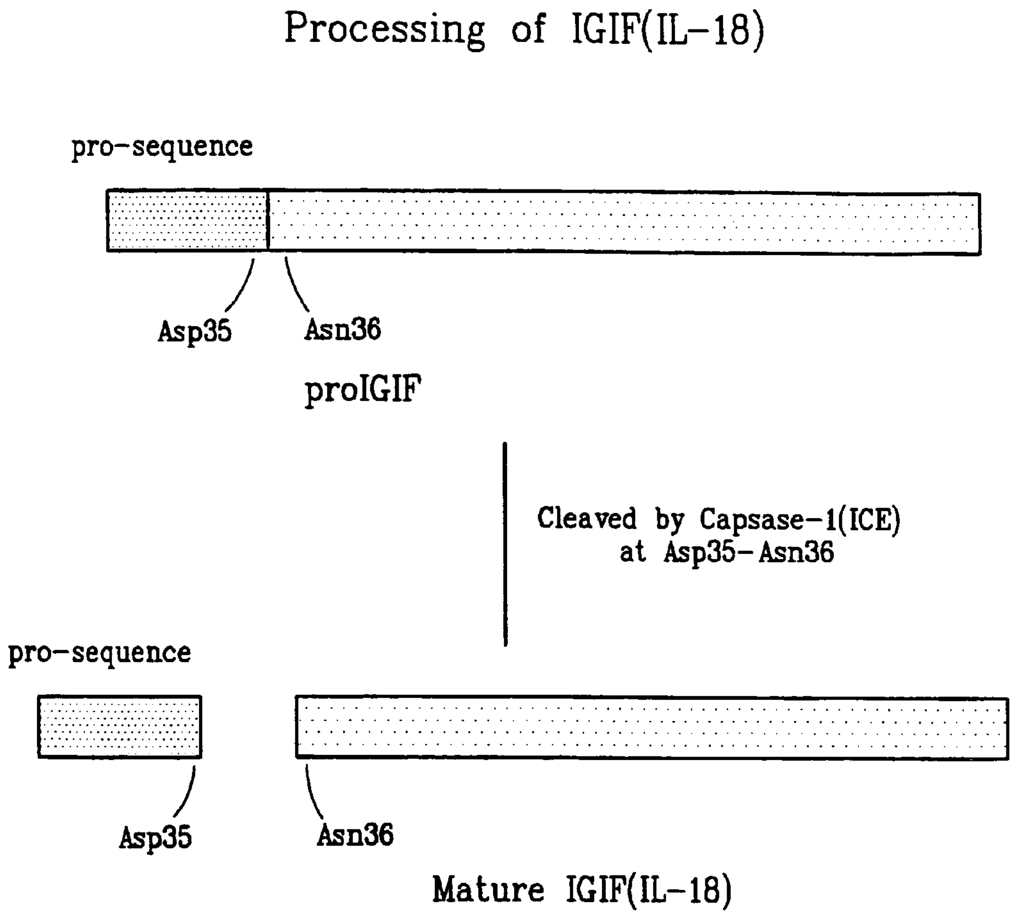
FIGS. 1A and 1B depict preprocessed and mature IL-18 as discussed in Example 2.

The invention arises from the discovery that particular proteins enhance and/or modulate the immune response. Accordingly, such proteins may be delivered as immunotherapeutics or as components in a vaccine.

As used herein, the term "immunomodulating proteins" is meant to refer to proteins and nucleic acid molecule expression products according to the present invention which enhance and/or modulate the immune response. Accordingly, immunomodulating proteins may be delivered as immunotherapeutics or as components in a vaccine.

Immunomodulating proteins include chemokines, adhesion molecules, cytokines, co-stimulatory molecules, growth factors, and receptor molecules.

Chemokines that are immunomodulating proteins include MIP-1$\alpha$, MIP-1$\beta$, RANTES, IL-8 and MCP-1.

Adhesion molecules that are immunomodulating proteins include members of the selectin family, mucin-like molecules, members of the integrin family, and members of the immunoglobulin superfamily.

Members of the selectin family that are immunomodulating proteins include L-selectin, P-selectin and E-selectin.

Mucin-like molecules are ligands to members of the selectin family. Mucin-like molecules that are immunomodulating proteins include CD34, GlyCAM-1 and MAdCAM-1.

Members of the integrin family that are immunomodulating proteins include LFA-1, VLA-1 Mac-1 and p150.95.

Members of the immunoglobulin superfamily that are immunomodulating proteins include PECAM, ICAMs, ICAM-1, ICAM-2, ICAM-3, CD2 and LFA-3.

Cytokines that are immunomodulating proteins include M-CSF, GM-CSF, G-CSF, CSF, IL-4, and mutant forms of IL-18 which include a deletion of the first about 35 amino acid residues present on the pro-form of the protein but not the mature form.

Co-stimulatory molecules that are immunomodulating proteins include CD40 and CD40 ligand (CD40L).

Growth factors that are immunomodulating proteins include vascular growth factor, IL-7, nerve growth factor and vascular endothelial growth factor.

Receptor molecules that are immunomodulating proteins include Fas "death gene" expression product, tumor necrosis factor TNF receptor, Flt, Apo-1, p55, WSL-1, DR3, TRAMP, Apo-3, AIR, LARD, NGRF, DR4, DR5, KILLER, TRAIL-R2, TRICK2, DR6; others include Caspase (ICE).

Other molecules include Caspase-1 (ICE).

According to some embodiments of the invention, an immunomodulating protein is delivered by administering a nucleic acid molecule which, when taken up by a cell, is expressed to produce the immunomodulating protein. According to some embodiments of the invention, the immunomodulating protein is delivered by administering the protein itself. According to some embodiments of the invention, the immunomodulating protein is delivered by administering either nucleic acid molecules or protein. According to some embodiments of the invention, the immunomodulating protein is delivered by administering both nucleic acid molecules and proteins simultaneously.

According to some embodiments of the invention, the immunomodulating protein, either as a protein or a nucleic acid molecule encoding the protein, is administered as a component of or otherwise as a supplement to in conjunction with a vaccine composition. The vaccine may be either a subunit vaccine, a killed vaccine, a live attenuated vaccine, a cell vaccine, a recombinant vaccine or a nucleic acid or DNA vaccine. In the case of a live attenuated vaccine, a cell vaccine, a recombinant vaccine or a nucleic acid or DNA vaccine, the immunomodulating protein may be encoded by the nucleic acid molecules of these vaccines.

Immunomodulating proteins are useful to induce and enhance cytotoxic T cell (CTL) responses, and/or induce and enhance antibody responses, and/or induce and enhance T cell proliferation responses.

Immunomodulating proteins that induce and enhance CTL responses are particularly useful when administered in conjunction or as part of a vaccine against an intracellular pathogens, or against cells associated with autoimmune disease or cancer. Immunomodulating proteins that induce and enhance CTL responses are particularly useful when administered in conjunction with live attenuated vaccines, cell vaccines, recombinant vaccines, and nucleic acid/DNA vaccines. Alternatively, immunomodulating proteins that induce and enhance CTL responses are useful as immunotherapeutics which are administered to patients suffering from cancer or intracellular infection. Immunomodulating proteins that induce and enhance CTL responses are useful when administered to immunocompromised patients.

Immunomodulating proteins that induce and enhance antibody responses are particularly useful when administered in conjunction or as part of a vaccine against bacteria, other extracellular pathogens, or those viruses for which antibody responses are protective such as hepatitis B virus. Immunomodulating proteins that induce and enhance antibody responses are particularly useful when administered in conjunction with subunit vaccines. Alternatively, immunomodulating proteins that induce and enhance antibody responses are useful as immunotherapeutics which are administered to patients suffering from undesirable CTL immune responses. Such shifting of the patient's immune system reduces the pathology caused by the CTL response. Immunomodulating proteins that induce and enhance antibody responses are useful when administered to immunocompromised patients.

Immunomodulating proteins that induce and enhance T cell proliferation responses are particularly useful when administered in conjunction or as part of vaccines. Alternatively, immunomodulating proteins that induce and enhance T cell proliferation responses are useful as immunotherapeutics. Immunomodulating proteins that induce and enhance T cell proliferation responses are useful when administered to immunocompromised patients.

Chemokines:

The administration of chemokines or nucleic acid molecules that encode chemokines results in an increased expression of chemokines by cells.

MCP-1 is particularly useful in inducing and enhancing CD8+ CTLs.

MIP-1α is particularly useful in the induction of antibodies.

IL-8 is particularly useful in the induction of antibodies, and is a strong inducer of T helper responses.

RANTES induces TH1 as well as CTL responses.

MIP-1β, such as the construct which is been cloned into pCDNA3 to generate pCDNA3-MIP-1β, may also be used.

Adhesion Molecules:

Members of the Selectin Family

L-selectin

P-selectin

E-selectin.

Mucin-Like Molecules

CD34

GlyCAM-1 such as the construct which has been cloned into pCDNA3 to generate pCDNA3-GlyCAM-1

MadCAM-1.

Members of the Integrin Family

LFA-1

VLA-1

Mac-1 p150.95

Members of the Immunoglobulin Superfamily

PECAM

ICAMs

ICAM-1

ICAM-2

ICAM-3

CD2

LFA-3.

Adhesion molecules are most useful when administered as nucleic acid molecules.

Adhesion molecules are most useful when administered as nucleic acid molecules as part of or in conjunction with vaccines, particularly live attenuated vaccines, cell vaccines, recombinant vaccines, and nucleic acid/DNA vaccines.

Adhesion molecules useful when delivered as nucleic acid molecules intratumor or intralesion.

Preferred adhesion molecules include ICAM-1, LFA-3 and E-selectin.

ICAM-1 is best for CTL and proliferation.

Cytokines
- M-CSF
- G-CSF
- CSF
- IL-4
- mutant forms of IL-18

Co-Stimulatory Molecules
- CD40 such as the construct in which cDNA encoding CD40 is cloned into pCDNA3 to generate pCDNA3-CD40 may be used
- CD40L Growth Factors
- vascular growth factor such as the construct in which cDNA encoding vascular growth factor is cloned into pCDNA3 to generate pCDNA3-VGF may be used
- IL-7
- nerve growth factor
- vascular endothelial growth factor Receptor Molecules
- Fas "death gene" expression product
- TNF receptor
- Flt
- Apo-1
- p55
- WSL-1
- DR3
- TRAMP
- Apo-3
- AIR
- LARD
- NGRF
- DR4
- DR5
- KILLER
- TRAIL-R2
- TRICK2
- DR6

Other
- Caspase (ICE)

Table 1 lists the GENBANK Accession numbers and journal citations for the nucleotide and amino acid sequences for each of the above immunomodulating proteins and for CD86 (B7.2).

DNA vaccines are described in PCT/US90/01515, PCT/US93/02338, PCT/US93/048131, and PCT/US94/00899, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

Some aspects of the present invention relate to methods of introducing genetic material into the cells of an individual in order to induce immune responses against proteins and peptides which are encoded by the genetic material. The methods comprise the steps of administering to the tissue of said individual, either a single nucleic acid molecule that comprises a nucleotide sequence that encodes a desired peptide or protein and a nucleotide sequence that encodes an immunomodulating protein, or a composition having two nucleic acid molecules, one that comprises a nucleotide sequence that encodes a desired peptide or protein and one that comprises a nucleotide sequence that encodes an immunomodulating protein. The nucleic acid molecule(s) may be provided as plasmid DNA, the nucleic acid molecules of recombinant vectors or as part of the genetic material provided in an attenuated vaccine or cell vaccine. Alternatively, in some embodiments, the immunomodulating protein may be delivered as a protein.

According to some embodiments, combinations of two or more immunomodulating proteins are administered to an individual. In some embodiments, genes encoding a combination of two or more immunomodulating proteins are administered to an individual together with a gene that encodes an immunogen and/or an immunogenic protein as part of a vaccine protocol. In some embodiments, a combination of an immunomodulating protein and a gene encoding an immunomodulating proteins is administered to an individual together with a gene that encodes an immunogen and/or an immunogenic protein as part of a vaccine protocol. In some embodiments, a combination of two or more immunomodulating proteins is administered to an individual together with a gene that encodes an immunogen and/or an immunogenic protein as part of a vaccine protocol.

According to some embodiments, immunomodulating proteins are administered to an individual in combination with the costimulatory molecule CD86 (B7.2). In some embodiments, genes encoding a combination of CD86 and one or more immunomodulating proteins are administered to an individual together with a gene that encodes an immunogen and/or an immunogenic protein as part of a vaccine protocol. In some embodiments, a combination of CD86 protein and a gene encoding an immunomodulating proteins is administered to an individual together with a gene that encodes an immunogen and/or an immunogenic protein as part of a vaccine protocol. In some embodiments, a combination of immunomodulating protein and a gene encoding CD86 protein is administered to an individual together with a gene that encodes an immunogen and/or an immunogenic protein as part of a vaccine protocol. In some embodiments, a combination of CD86 and one or more immunomodulating proteins is administered to an individual together with a gene that encodes an immunogen and/or an immunogenic protein as part of a vaccine protocol. In some embodiments, genes encoding a combination of CD86 and one or more chemokines and/or adhesion molecules are administered to an individual together with a gene that encodes an immunogen and/or an immunogenic protein as part of a vaccine protocol. In some embodiments, genes encoding a combination of CD86 and ICAM-1 are administered to an individual together with a gene that encodes an immunogen and/or an immunogenic protein as part of a vaccine protocol.

According to some aspects of the present invention, compositions and methods are provided which prophylactically and/or therapeutically immunize an individual against a pathogen or abnormal, disease-related cell. The genetic material that encodes a peptide or protein that shares at least an epitope with an immunogenic protein found on the pathogen or cells to be targeted and genetic material that encodes an immunomodulating protein. Alternatively, in some embodiments, the immunomodulating protein may be delivered as a protein.

The genetic material is expressed by the individual's cells and serves as an immunogenic target against which an immune response is elicited. The resulting immune response is broad based: in addition to a humoral immune response, both arms of the cellular immune response are elicited. The methods of the present invention are useful for conferring prophylactic and therapeutic immunity. Thus, a method of immunizing includes both methods of immunizing against immunogens and thus for example of protecting an individual from pathogen challenge, or occurrence or proliferation of specific cells as well as methods of treating an individual suffering from pathogen infection, hyperproliferative disease or autoimmune disease.

As used herein the term "target protein" is meant to refer to peptides and protein encoded by gene constructs of the present invention which act as target proteins for an immune response. The term "target protein" and "immunogen' are used interchangeably and refer to a protein against which an immune response can be elicited. The target protein is an immunogenic protein which shares at least an epitope with a protein from the pathogen or undesirable cell-type such as a cancer cell or a cell involved in autoimmune disease against which immunization is required. The immune response directed against the target protein will protect the individual against and treat the individual for the specific infection or disease with which the target protein is associated.

The present invention is useful to elicit broad immune responses against a target protein, i.e. proteins specifically associated with pathogens, allergens or the individual's own "abnormal" cells. The present invention is useful to immunize individuals against pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

According to some aspects of the present invention, DNA or RNA that encodes a target protein and an immunomodulating protein is introduced into the cells of tissue of an individual where it is expressed, thus producing the target protein. The DNA or RNA sequences encoding the target protein and immunomodulating protein are linked to regulatory elements necessary for expression in the cells of the individual. Regulatory elements for DNA expression include a promoter and a polyadenylation signal. In addition, other elements, such as a Kozak region, may also be included in the genetic construct.

As used herein, the term "genetic construct" refers to the DNA or RNA molecules that comprise a nucleotide sequence which encodes the target protein and which includes initiation and termination signals operably linked to regulatory elements including a promoter and polyadenylation signal capable of directing expression in the cells of the vaccinated individual and/or a nucleotide sequence which encodes the immunomodulating protein and which includes initiation and termination signals operably linked to regulatory elements including a promoter and polyadenylation signal capable of directing expression in the cells of the vaccinated individual. In some embodiments, expressible forms sequences that encode the target protein and expressible forms sequences that encode an immunomodulating protein are found on the same nucleic acid molecule that is delivered to the individual. In some embodiments, expressible forms sequences that encode the target protein occur on separate same nucleic acid molecule from the nucleic acid molecules that contain expressible forms sequences that encode an immunomodulating protein. In such cases, both molecules are delivered to the individual.

As used herein, the term "expressible form" refers to gene constructs which contain the necessary regulatory elements operable linked to a coding sequence that encodes a target protein or an immunomodulating protein, such that when present in the cell of the individual, the coding sequence will be expressed.

As used herein, the term "sharing an epitope" refers to proteins which comprise at least one epitope that is identical to or substantially similar to an epitope of another protein.

As used herein, the term "substantially similar epitope" is meant to refer to an epitope that has a structure which is not identical to an epitope of a protein but nonetheless invokes an cellular or humoral immune response which cross reacts to that protein.

Genetic constructs may comprise a nucleotide sequence that encodes a target protein or an immunomodulating protein operably linked to regulatory elements needed for gene expression. According to the invention, combinations of gene constructs which include one that comprises an expressible form of the nucleotide sequence that encodes a target protein and one that includes an expressible form of the nucleotide sequence that encodes an immunomodulating protein are provided. Incorporation into a living cell of the DNA or RNA molecule(s) which include the combination of gene constructs results in the expression of the DNA or RNA and production of the target protein and the immunomodulating protein. An enhanced immune response against the target protein results.

When taken up by a cell, the genetic construct(s) may remain present in the cell as a functioning extrachromosomal molecule and/or integrate into the cell's chromosomal DNA. DNA may be introduced into cells where it remains as separate genetic material in the form of a plasmid or plasmids. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal.

Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to bovine growth hormone polyadenylation signal, SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration. In some embodiments, the cDNA encoding the immunomodulating protein is inserted into pCDNA3.

In some preferred embodiments related to immunization applications, nucleic acid molecule(s) are delivered which include nucleotide sequences that encode a target protein, the immunomodulating protein and, additionally, genes for proteins which further enhance the immune response against such target proteins. Examples of such genes are those which encode other cytokines and lymphokines such as α-interferon, gamma-interferon, platelet derived growth factor (PDGF), TNF, epidermal growth factor (EGF), IL-1, IL-2, IL-4, IL-6, IL-8, IL-10 and IL-12. In some embodiments, it is preferred that the gene for GM-CSF is included in genetic constructs used in immunizing compositions.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs which are functional in the cells.

Routes of administration include, but are not limited to, intramuscular, intranasally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include to mucosal tissue, intramuscular, intraperitoneal, intradermal and subcutaneous injection. Genetic constructs may be administered by means including, but not limited to, traditional syringes, needleless injection devices, or "microprojectile bombardment gene guns".

The pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 micrograms DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vaso-constriction agent is added to the formulation.

In some embodiments, the nucleic acid molecule is delivered to the cells in conjunction with administration of a polynucleotide function enhancer or a genetic vaccine facilitator agent. Polynucleotide function enhancers are described in U.S. Ser. No. 08/008,342 filed Jan. 26, 1993, U.S. Ser. No. 08/029,336 filed Mar. 11, 1993, U.S. Ser. No. 08/125,012 filed Sep. 21, 1993, and International Application Serial Number PCT/US94/00899 filed Jan. 26, 1994, which are each incorporated herein by reference. Genetic vaccine facilitator agents are described in U.S. Ser. No. 08/221,579 filed Apr. 1, 1994, which is incorporated herein by reference. The co-agents which are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with a GVF include growth factors, cytokines and lymphokines such as α-interferon, gamma-interferon, platelet derived growth factor (PDGF), TNF, epidermal growth factor (EGF), IL-1, IL-2, IL-4, IL-6, IL-8, IL-10 and IL-12 as well as fibroblast growth factor, surface active agents such as immune-stimulating complexes (ISCOMS), Freund's incomplete adjuvant, LPS analog including monophosphoryl Lipid A (MPL), muramyl peptides, quinone analogs and vesicles such as squalene and squalene, and hyaluronic acid may also be used administered in conjunction with the genetic construct. In some embodiments, an immunomodulating protein may be used as a GVF.

Nucleic acid molecules which are delivered to cells according to the invention may serve as genetic templates for proteins that function as prophylactic and/or therapeutic immunizing agents. In preferred embodiments, the nucleic acid the nucleic acid molecules comprise the necessary regulatory sequences for transcription and translation of the coding region in the cells of the animal.

The present invention may be used to immunize an individual against all pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhoea, *listeria* and *shigella*. In addition, the present invention is also useful to immunize an individual against protozoan pathogens which include a stage in the life cycle where they are intracellular pathogens. As used herein, the term "intracellular pathogen" is meant to refer to a virus or pathogenic organism that, at least part of its reproductive or life cycle, exists within a host cell and therein produces or causes to be produced, pathogen proteins. Table 2 provides a listing of some of the viral families and genera for which vaccines according to the present invention can be made. DNA constructs that comprise DNA sequences which encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 3.

In order to produce a genetic vaccine to protect against pathogen infection, genetic material which encodes immunogenic proteins against which a protective immune response can be mounted must be included in a genetic construct as the coding sequence for the target. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The genetic construct used in the genetic vaccine can include genetic material which encodes many pathogen antigens. For example, several viral genes may be included in a single construct thereby providing multiple targets.

Tables 2 and 3 include lists of some of the pathogenic agents and organisms for which genetic vaccines can be prepared to protect an individual from infection by them. In some preferred embodiments, the methods of immunizing an individual against a pathogen are directed against HIV, HTLV or HBV.

Another aspect of the present invention provides a method of conferring a broad based protective immune response against hyperproliferating cells that are characteristic in hyperproliferative diseases and to a method of treating individuals suffering from hyperproliferative diseases. As used herein, the term "hyperproliferative diseases" is meant to refer to those diseases and disorders characterized by xr hyperproliferation of cells. Examples of hyperproliferative diseases include all forms of cancer and psoriasis.

It has been discovered that introduction of a genetic construct that includes a nucleotide sequence which encodes an immunogenic "hyperproliferating cell" associated protein into the cells of an individual results in the production of those proteins in the vaccinated cells of an individual. As used herein, the term "hyperproliferative-associated protein" is meant to refer to proteins that are associated with a hyperproliferative disease. To immunize against hyperproliferative diseases, a genetic construct that includes a nucleotide sequence which encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF. In addition to oncogene products as target antigens, target proteins for anti-cancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins which are found at higher levels in tumor cells including the protein recognized by monoclonal antibody 17-1A and folate binding proteins.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include Vβ-3, Vβ-14, Vβ-17 and Vα-17. Thus, vaccination with a DNA construct that encodes at least one of these proteins will elicit an immune response that will target T cells involved in RA. See: Howell, M. D., et al., 1991 *Proc. Natl. Acad. Sci. USA* 88:10921-10925; Paliard, X., et al., 1991 *Science* 253:325-329; Williams, W. V., et al., 1992 *J. Clin. Invest.* 90:326-333; each of which is incorporated herein by reference.

In MS, several specific variable regions of TCRs which are involved in the disease have been characterized. These TCRs include Vβ-7 and Vα-10. Thus, vaccination with a DNA construct that encodes at least one of these proteins will elicit an immune response that will target T cells involved in MS. See: Wucherpfennig, K. W., et al., 1990 *Science* 248:1016-1019; Oksenberg, J. R., et al., 1990 *Nature* 345:344-346; each of which is incorporated herein by reference.

In scleroderma, several specific variable regions of TCRs which are involved in the disease have been characterized. These TCRs include Vβ-6, Vβ-8, Vβ-14 and Vα-16, Vα-3C, Vα-7, Vα-14, Vα-15, Vα-16, Vα-28 and Vα-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al. 1987 *Sequence of Proteins of Immunological Interest* U.S. Department of Health and Human Services, Bethesda Md., which is incorporated herein by reference. In addition, a general method for cloning functional variable regions from antibodies can be found in Chaudhary, V. K., et al., 1990 *Proc. Natl. Acad. Sci. USA* 87:1066, which is incorporated herein by reference.

In addition to using expressible forms of immunomodulating protein coding sequence to improve genetic vaccines, the present invention relates to improved attenuated live vaccines and improved vaccines which use recombinant vectors to deliver foreign genes that encode antigens. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, which are each incorporated herein by reference. Gene constructs are provided which include the nucleotide sequence that encodes an immunomodulating protein is operably linked to regulatory sequences that can function in the vaccine to effect expression. The gene constructs are incorporated in the attenuated live vaccines and recombinant vaccines to produce improved vaccines according to the invention.

The present invention provides an improved method of immunizing individuals that comprises the step of delivering gene constructs to the cells of individuals as part of vaccine compositions which include are provided which include DNA vaccines, attenuated live vaccines and recombinant vaccines. The gene constructs comprise a nucleotide sequence that encodes an immunomodulating protein and that is operably linked to regulatory sequences that can function in the vaccinee to effect expression. The improved vaccines result in an enhanced cellular immune response.

Another aspect of the present invention relates to the use of either GM-CSF or a nucleic acid molecule encoding GM-CSF or both in combination with a DNA vaccine for which a strong antibody response or helper T cell response is particularly desirable. One example of such a vaccine is a vaccine against hepatitis B. Other examples include extracellular pathogens and allergens. The administration of either GM-CSF or a nucleic acid molecule encoding GM-CSF or both in combination with a DNA vaccine is also useful for vaccinated individuals identified as being immunocompromised.

Another embodiment of the present invention relates to the use of anti-chemokine antibodies to treat patients who have autoimmune diseases. Autoimmune diseases are outlined above. Anti-chemokine antibodies include antibodies specific for MCP-1, MIP-1α, MIP-1β, IL-8 or RANTES. Anti-chemokine antibodies may be administered to patients suspected of suffering form such diseases in therapeutically effective amounts to reduce or alleviate symptoms.

Pharmaceutical compositions for treating autoimmune disease comprise an antibody specific for a chemokine and a pharmaceutically acceptable carrier. According to preferred embodiments, the compositions are injectable. The sterile, pyrogen-free, particulate-free injectable compositions comprise one or more an antibody specific for a chemokine and a pharmaceutically acceptable carrier or injection vehicle.

The antibodies are made according to conventional methods for producing monoclonal antibodies. The carrier be selected from those well known to persons having ordinary skill in the art. An example of a carrier is sterile saline.

Those having ordinary skill in the art can produce monoclonal antibodies which specifically bind to a MCP-1, MIP-1α, MIP-1β, IL-8 or RANTES using standard techniques and readily available starting materials. The techniques for producing monoclonal antibodies are outlined in Harlow, E. and D. Lane, (1988) *ANTIBODIES: A Laboratory Manual*, Cold Spring Harbor Laboratory, Cold Spring Harbor N.Y., which is incorporated herein by reference, provide detailed guidance for the production of hybridomas and monoclonal antibodies which specifically bind to target proteins.

Briefly, the chemokine is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the protein of interest, the hybridoma which produces them is cultured to produce a continuous supply of antigen specific antibodies.

According to the present invention, antibodies specific for MCP-1, MIP-1α, MIP-1β, IL-8 or RANTES may be used to treat an autoimmune disease. Accordingly, MCP-1, MIP-1α, MIP-1β, IL-8 or RANTES is used to generate hybridomas. The genes which encode these proteins are widely known and readily available to those having ordinary skill in the art. Thus, one having ordinary skill in the art can make antibodies useful to practice the present invention. In addition to rodent antibodies, the present invention relates to human antibodies, humanized antibodies, Fabs and chimeric antibodies and Fabs which bind to MCP-1, MIP-1α, MIP-1β, IL-8 or RANTES which may be produced routinely by those having ordinary skill in the art.

Those having ordinary skill in the art can readily identify individuals who suffer form or are susceptible to an autoimmune disease.

The compositions may include additional components to render them more effective. For example, a composition of the invention may comprise multiple anti-chemokine antibodies including antibodies specific for different chemokines and antibodies specific for different epitopes of the same chemokine.

About 5 μg to 5000 mg of antibody may be administered. In some preferred embodiments, 50 μg to 500 mg of antibody may be administered. In other preferred embodiments, 500 μg to 50 mg of antibody may be administered. In a preferred embodiment, 5 mg of antibody is administered.

Compositions may be administered by an appropriate route such as, for example, by oral, intranasal, intramuscular, intraperitoneal or subcutaneous administration. In some embodiments, intravenous administration is preferred.

Subsequent to initial administration, individuals may be boosted by readministration. In some preferred embodiments, multiple administrations are performed.

EXAMPLES

Example 1

Introduction

To molecularly dissect the specific roles of chemokines in immune response we cloned cDNAs encoding the α-chemokine IL-8 as well as cDNAs encoding the β-chemokines MIP-1α, RANTES, and MCP-1 individually into expression vectors and co-immunized them along with DNA immunogens which encodes for HIV-1 envelope or gag/pol proteins. Using these DNA vaccine constructs as model antigens, we examined the specific roles of the expression of chemokine genes play in the development of the immune responses through analyzing the antigen-specific humoral and cell-mediated immune responses induced following such immunization. We observed that chemokines had specific, identifiable roles in the activation and modulation of antigen-specific immune responses.

Results

Induction of Chemokines by DNA Vaccination

Mice were immunized with 50 μg of pCDNA3 (control), pCEnv, or pCGag/pol. After two weeks, the mice were sacrificed, their spleens were harvested, and their lymphocytes were isolated. These cells were stimulated in vitro by antigen-specific stimulation (using fixed recombinant vaccinia infected stimulator cells) for 5 days. We collected the culture supernatant from the effector cells and tested them for the release of chemokines MIP1-α, MIP1-β, and RANTES. We observed that DNA immunization with pCEnv or pCGag/pol induced significantly greater levels of expression of β-chemokines MIP1-α, MIP1-β, and RANTES over those of control vector. The increase was present as early as 2 weeks following the first immunization, suggesting that β chemokines could be modulating immune responses in vivo. To determine the effects of the chemokines on antigen specific responses we next investigated their effects on immune responses induced by the DNA vaccine.

Construction of Chemokine Expression Cassettes

The genes for chemokines IL-8, MIP1-α, MCP-1α, MCP-1, and RANTES were individually cloned into pCDNA3 plasmid expression vectors using methods described in Kim, J. J., D. B. Weiner (1997) Springer Sem Immunopathol 19 174-195; Kim, J. J., et al. (1997) Nature Biot. 15, 641-645; and Kim, J. J., et al. (1997) J. Immunol. 158, 816-826, which are each incorporated herein by reference. These chemokine expression cassettes were verified by sequencing analysis of the entire insert (including both 5' and 3' flanking sequences). In addition, these chemokine constructs were transfected in vitro into RD cells and the expression of these constructs were verified by immunoprecipitation using relevant antibodies or by chemokine ELISA. The expression constructs for IL-8, MIP1-α, MCP-1, and RANTES were also used as vaccines and immunized into mice. It was determined by the in vivo expression technique described in Materials and Methods that these constructs expressed their encoded chemokines in vivo in mouse muscle tissue.

IL-8 is a Strong Inducer of T Helper Response

The effects of various chemokines on vaccine induced responses were analyzed individually. Antisera from pCEnv and pCEnv+IL-8 immunized mice were collected and analyzed for specific antibody responses against HIV-1 gp120 protein by ELISA. The gp120-specific antibody titer from sera collected at weeks 0, 2, 4, and 6 post-DNA immunization was measured. At 1:128 dilution, sera from the groups immunized with pCEnv+IL-8 showed antibody response against gp120 protein which was greater than that of the group immunized with pCEnv alone. A similar result was seen with the groups immunized with pCGag/pol. Furthermore, the subclasses of gp120-specific IgGs induced by the co-administration with IL-8 genes were determined. Production of IgG1 type is induced by Th2 type cytokines, whereas the IgG2a type production is induced by Th1 type cytokines. The relative ratios of IgG1 to IgG2a (Th2 to Th1) were measured. The pCEnv immunized group had a IgG1 to IgG2a ratio of 1.3. On the other hand, co-injection with pCEnv+IL-8 decreased the relative ratio to 0.9, indicating a shift to Th1-type response. IL-8 therefore influenced both the quality and quantity of the antigen-specific response.

The effect of IL-8 expression on T helper cell proliferative response was also examined. IL-8 co-expression with HIV-1 immunogens (pCEnv or pCGag/pol) resulted in a dramatic level of antigen-specific T helper cell proliferative responses. The increase in proliferation was between 4 and 6 fold, a significant increase in antigen-specific responses. In addition, the effect of IL-8 co-expression on the induced CTL response was also investigated. A background level of specific killing was observed from the control animals, whereas the animals immunized with pCEnv alone showed a small, but consistent level of CTL response. IL-8 co-administration did not have any enhancement effect on the antigen-specific CTL response. Similar CTL results were observed from pCGag/pol+IL-8 co-immunization.

Cytokines play a key role in directing and targeting immune cells during immune response. For instance, IFN-γ is intricately involved in the regulation of T cell-mediated cytotoxic immune responses while IL-4 plays a dominant role in B cell-mediated immune responses. TNF-α is produced by activated macrophages and monocytes, neutrophils, activated lymphocytes, and NK cells and has been suggested to play a pivotal role in regulating the synthesis of other proinflammatory cytokines. We analyzed supernatant from the effector cells stimulated in vitro for CTL assay and tested them for the release of cytokines IFN-γ, IL-4, and TNF-α. We found that IL-8 expression increased the level of IFN-γ only slightly, but it did not affect the levels of cytokines IL-4 and TNF-α. This is somewhat surprising as the dramatic effect of IL-8 co-delivery on the humoral responses might have been expected to have a noticeable effect on IL-4. However, this was not observed.

MIP1-α is a Strong Inducer of Antibody Response

MIP1-α co-expression exhibited a more drastic effect than IL-8 in the induction of antigen-specific humoral response. PCEnv+MIP1-αco-immunization resulted in a dramatic enhancement of envelope-specific antibody response. A similar result was seen with the groups immunized with pCGag/pol. The relative ratios of IgG1 to IgG2a following the co-administration with pCEnv+MIP1-α were determined. The pCEnv immunized group had a IgG1 to IgG2a ratio of 1.3. On the other hand, co-injection with pCEnv+MIP1-α decreased the relative ratio to 1.7, indicating a shift to Th2-type response. MIP1-αco-expression with HIV-1 immunogens (pCEnv or pCGag/pol) resulted in enhancement of antigen-specific T helper cell proliferative responses. In contrast, MIP1-α immunization had minimal effect on the antigen-specific CTL responses or the induction of cytokines. Again, as was observed in the analysis of IL-8, effects on cytokine production, no effect was noted on IL-4 levels.

RANTES Induces Th1 as Well as CTL Responses

We next examined the effects of RANTES co-delivery on vaccine induced immune responses. Unlike IL-8 or MIP1-α, co-expression of RANTES with pCEnv did not enhance HIV-1 envelope-specific antibody response. In addition, pCEnv-RANTES co-immunization did not have any effect on the IgG1-IgG2a ratio when compared to the group immunized with pCEnv alone. In contrast to the antibody responses, RANTES co-vaccinating with HIV-1 immunogens (pCEnv or pCGag/pol) resulted in significant augmentation of antigen-specific T helper cell proliferative responses. Furthermore, two times higher level expressions of Th1 cytokines IFN-γ and TNF-α were observed from the group co-administered with pCEnv+RANTES. Unlike co-injection with PCEnv+IL-8 or pCEnv-MIP-1α which resulted in a minimal effect in CTL activity, a more dramatic increase in the specific killing of targets infected with vaccinia (vMN462) expressing HIV-1 envelope was observed after co-injection with pCEnv+RANTES. Greater than 36% specific lysis of target cells was observed after co-injection with pCEnv+RANTES at a 50:1 effector to target (E:T) ratio. Similarly, the mice immunized with pCGag/pol+RANTES resulted in a significant enhancement of antigen-specific CTL lysis of targets infected with vaccinia (vVK1) expressing HIV-1 gag/pol. RANTES co-delivery appeared to polarize the resulting responses towards a Th1 type phenotype as no effect on IL-4 was again noted.

MCP-1 Induces CTL Responses

Adjuvant properties of MCP-1 cDNA was next observed. MCP-1 appeared to have a minimal effect on the specific antibody binding profile induced by pCEnv immunization. Moreover, MCP-1 co-expression with HIV-1 immunogens (pCEnv or pCGag/pol) had positive, but relatively minor (two fold) enhancement of antigen-specific T. Helper cell proliferative responses. The relative ratios of IgG1 to IgG2a following the co-administration with pCEnv+MCP-1 were determined. The pCEnv immunized group had a IgG1 to IgG2a ratio of 1.3. On the other hand, co-injection with pCEnv+MCP-1 decreased the relative ratio to 1.0, indicating a shift to Th1-type response. A more dramatic increase in the specific killing was observed after co-injection with pCEnv+MCP-1. Greater than 36% specific lysis of target cells was observed after co-injection with pCEnv+MCP-1 at a 50:1 effector to target (E:T) ratio. Similarly, the mice immunized with pCGag/pol_MCP-1 resulted in a significant enhancement of antigen-specific CTL lysis of HIV-1 gag/pol expressing targets. The level of IFN-γ release by mice immunized with pCEnv+MCP-1 was significantly greater than those of the pCEnv immunized or the control groups. Again, the level of IL-4 released from all groups were similar. Moreover, the level of TNF-α release by pCEnv+MCP-1 immunized group was significantly greater than those of the pCEnv immunized or the control groups. These cytokine release data support our CTL results which elucidate the roles of MCP-1 in the activation of $CD8^+$ CTL.

Determination of CD8 Restriction in CTL Response

To determine whether the increases in CTL response via co-expression on MCP-1 and RANTES was restricted to $CD8^+$ T cells, CTL assays were performed using a HIV-1 envelope peptide (RIHIGPGRAFYTTKN, SEQ ID NO:1) which has been shown to be a specific epitope for MHC class I-restricted CTL for balb/c mice. Mice received two immunizations of 50 μg of each DNA construct separated by two weeks and their spleens were harvested one week after the second immunization. The CTL assay was performed on the splenocytes following in vitro stimulation with envelope-specific peptides. We observed a significant enhancement of CTL response after both co-injection with MCP-1 and RANTES at 35% and 26% specific killing at an E:T ratio of 50:1, respectively. We verified this observation by measuring CTL activity after the removal of $CD8^+$ T cells from the effector cell population by complement lysis. The removal of $CD8^+$ T cells resulted in the suppression of antigen-specific CTL enhancement observed after co-injections with MCP-1 and RANTES. These results indicate that the enhancement of cytolytic activity was antigen-specific, class I-restricted CD+ T cell dependent.

Enhancement of Chemokine Expression

It was important to determine the effects, if any, of those specific chemokine adjuvanted immunogens on chemokine production itself. We examined the expression of chemokines MIP1-α, MIP1-β, RANTES, and MCP-1 by stimulated cells collected from immunized animals. Chemokine co-injection modulated chemokine production in chemokine specific patterns. We made several important observations. Furthermore, we observed that co-immunization with chemokine genes resulted in increased expression of chemokines by the stimulated cells. For instance, we observed that MIP1-αexpression could be enhanced dramatically by co-immunization with pCEnv+MIP1-α over the level expressed by pCEnv immunization alone. In addition, we found that MIP1-β expression was dramatically enhanced by pCEnv+MCP-1 and pCEnv+RANTES immunization, the two most significant inducers of CTL responses. Moreover, pCEnv+MIP1-α, pCEnv+MCP- 1, and pCEnv+RANTES co-immunizations resulted in significant enhancement of RANTES expression by stimulated cells. Finally, the expression of MCP-1 was highest with pCEnv+MIP1-α and pCEnv+MCP-1 co-immunizations.

Discussion

The initiation of immune of inflammatory reactions is a complex process involving a tight coordinated expression of cellular adhesion molecules, cytokines, and chemokines. The chemokines are especially important in the molecular regulation of trafficking of leukocytes from the vessels to the peripheral sites of host defense. The superfamily of chemokines consists of any array of over 20 related proteins. Chemokines are broadly divided into three families, C-X-C (α), C-C(β), and C(γ), based on the presence and position of the conserved cysteine residues. In the members of the α family, the first two cysteines are separated by another amino acid, while those of the β family are placed next to each other. Only two members of the γ family have been identified so far, and both of them contain one instead of two cysteines in their N-terminus.

Members of each subfamily have unique as well as overlapping activities. While exact physiological and pathological functions are not yet clearly defined, certain simplifying generalities can be made from the literature. It has been reported that, in general, the members of the C-X-C family are chemoattractants and activators for polymorphonuclear leukocytes including neutrophils, eosinophils, and basophils. In contrast, the members of the C-C family serve as chemotactic factors to mononuclear cells such as monocytes and lymphoctyes. On the other hand, the C-X-C chemokines, IL-8 and IP-10, which are reportedly chemotactic to T-lymphocytes and C-C chemokines, MCP-1, MPC-3, RANTES, and MIP-1α w which are also chemotactic to basophils. In general, the function of chemokines appears to be recruitment and activation of leukocytes at the site of inflammation.

In addition their functions in inflammatory and immune responses, some chemokines play a critical role in the transmission and progression of HIV-1 and 2 viruses responsible for AIDS. It has been anticipated for oyer a decade that binding of HIV envelope glycoprotein gp120 to CD4 is not sufficient for viral fusion and entry, suggesting the requirement for an additional cell-surface cofactor for HIV infection. Recent studies have identified that the co-receptors required for the fusion of the T cell-tropic and macrophage-tropic viruses with their target cells to be CXCR-4 and CCR-5, respectively.

CXCR-4, also known as fusion or LESTR, was originally discovered as an orphan receptor with structural similarity to chemokine receptors. CXCR-4 was subsequently identified as a necessary cofactor for entry of T cell-tropic HIV viruses into $CD4^+$ cells. The β-chemokine SDF-1 is a ligand for CXCR-4 and a powerful inhibitor of infection by T cell-tropic HIV-1 strains. Similarly, the β-chemokines MIP-1α, MIP-1β, and RANTES are natural ligands for CCR-5 and are the major HIV suppressive factors produced by $CD8^+$ T cells for macrophage-tropic, but not T cell tropic, HIV isolates.

In these studies, a significant level of chemokine expression was observed following injection with a DNA immunogen. These results implied their potential roles as important activators and regulators of immune responses. To elucidate the specific roles of these chemokines in immune induction and modulation, we utilized the co-delivery of chemokine DNA expression cassettes as an antigen delivery model. DNA co-immunization is an appropriate model to investigate the in vivo functions of chemokines because DNA vaccines induce both humoral and cellular immune responses via both the MHC class I and II pathways. Furthermore, we and others have shown that antigen-specific immune responses to DNA vaccines can be modulated by the co-injection of costimulatory molecule and cytokine genes with DNA immunogen cassettes. Thus, we cloned and co-immunization chemokine expression vectors with HIV-1 DNA immunogens, and examined the effects of chemokine expression on immune activation. We observed that α-chemokine IL-8 and β-chemokines MIP-1α, RANTES, and MCP-1 had specific, identifiable roles in the activation of antigen-specific immune responses.

For instance, IL-8 is a chemotactic factor for neutrophils, inducing them to leave the bloodstream and migrate into the surrounding tissues. We observed that IL-8 was a strong inducer of $CD4^+$ T cells, indicated by strong T helper proliferative responses as well as the antibody responses. IL-8 co-expression also modulated the shift of immune responses to Th1-type, indicated by the reduction of IgG1 to IgG2a ratio and enhanced expression of IFN-γ. On the other hand, IL-8 co-administration did not have to noticeable effect on $CD8^+$ T cells, since it did not have any enhancement effect on the CTL response.

MIP-1α can chemoattractant and degranulate eosinophils. MIP-1α also induces histamine releases from basophils and mast cells, and is a chemotactic factor for basophils and B cells These reports support our observation that MIP-1α had the greatest effect on antibody responses. In addition, MIP-1α was also a strong inducer of CD4+ T cells, with good T helper proliferative responses. MIP-1α co-expression also modulated the shift of immune responses to Th2-type, indicated by the increases of IgG1 to IgG2a ratio. In contrast, MIP1-αco-immunization had minimal effect on the $CD8^+$ T cell response.

Unlike the effects of IL-8 and MIP-1α, RANTES co-immunization had minimal effect on antibody responses. RANTES is a monocyte chemoattractant. In addition, RANTES can chemoattract unstimulated $CD4^+$/$CD45RO^+$ memory T cells and stimulated $CD4^+$ and $CD8^+$ T cells. We observed that ability of RANTES to chemoattract $CD4^+$ and $CD8^+$ T cells to the site of DNA immunization served an important role in inducing T helper proliferative responses and CTL responses. The enhanced activation of Th1 responses was supported by the increased expression of Th1 cytokines IFN-γ and TNF-α. The high level of CTL responses induced by RANTES expression was determined to be class I-restricted and $CD8^+$ T cell dependent.

As a potent chemotactic factor for monocytes, MCP-1 is thought to be one of the most important chemokines for chronic inflammatory diseases. MCP-1 induces monocytes to migrate from the bloodstream to become tissue macrophages. MCP-1 was found to chemoattract T lymphocytes of the activated memory subset. Among all chemokines examined, MCP-1 is the most potent activator of CD8+ CTLs. The enhancement of CTL responses induced by MCP-1 expression was determined to be class 1-restricted and CD8+ T cell dependent. The enhanced CTL results are supported by increased expression to Th1 cytokines IFN-γ and TNF-α and the reduction of IgG11 to IgG2a ratio. Unlike RANTES, MCP-1 had positive, but moderate effect on the T helper cell proliferative responses. Like RANTES, MCP-1 co-administration had minimal effect on antibody responses. This comparison highlights that the induction of humoral, T helper, and T cytotoxic responses could be modulated independently of each other.

In addition to their direct effects on immune responses, co-expression of chemokine genes resulted in increased expression in autocrine manner. For instance, we observed that MIP1-αexpression could be enhanced dramatically by co-immunization with pCEnv+MIP1-α over the level expressed by pCEnv immunization alone. Similar increases in RANTES was observed from RANTES co-delivery and MCP-1 increased.

Furthermore, co-expression of chemokine also resulted in enhanced expression of other chemokines. These results imply that these chemokines not only have direct role in modulating immune responses, but they also act to control the production of other chemokines.

An important observation was the roles chemokine RANTES and MCP-1 play in inducing TNF-α expression. TNF-α is produced by activated macrophages and monocytes, neutrophils, activated lymphocytes, and NK cells whereas TNF-β is produced by lymphocytes. TNF-α is also implicated in septic shock following infection by Gram-negative bacteria and in rheumatoid arthritis. Furthermore, TNF-α plays a pivotal role in regulating the synthesis of other proinflammatory cytokines. Given TNF-α's critical roles in various ailments, there has been major efforts in reducing the level of TNF-α in vivo as potential treatment for conditions such as rheumatoid arthritis. In our experiments, we observed that co-expression of RANTES or MCP-1 resulted in the enhanced expression of TNF-α. These results imply that inhibiting RANTES and MCP-1 could compose a relevant strategy to curve TNF-α expression in vivo.

It is of interest that Th1 versus Th2 phenotype appears to segregate independently of other immune functions. IL-8 boosted humoral responses but drives those responses towards a Th1 phenotype, cutting the IgG1/IgG2a ratio in half. While MIP-1α, perhaps the most prolific driver of serology, skewed the IgG1/IgG2a ratio dramatically towards a Th2 response. It is clear that this manipulation can allow for induction of primary antigen-specific immune responses skewed towards a desired phenotype as well as immunoglobulin isotype independently of each other. Furthermore, the induction of cellular versus higher humoral responses appeared to be relatively polarized immune functions. Those chemokines with the most dramatic effect on humoral responses. IL-8 and MIP-1α, exhibited little effect on CTL responses whereas those which mediated the most dramatic effects on CTL responses, RANTES and MCP-1 had minimal effects on serology. The same CTL driving chemokines RANTES and MCP-1 both stimulated IFN-γ and TNF-α, while the humoral responders had minimal effects on these cytokine maker of immune activation.

Example 2

Figure 1B:
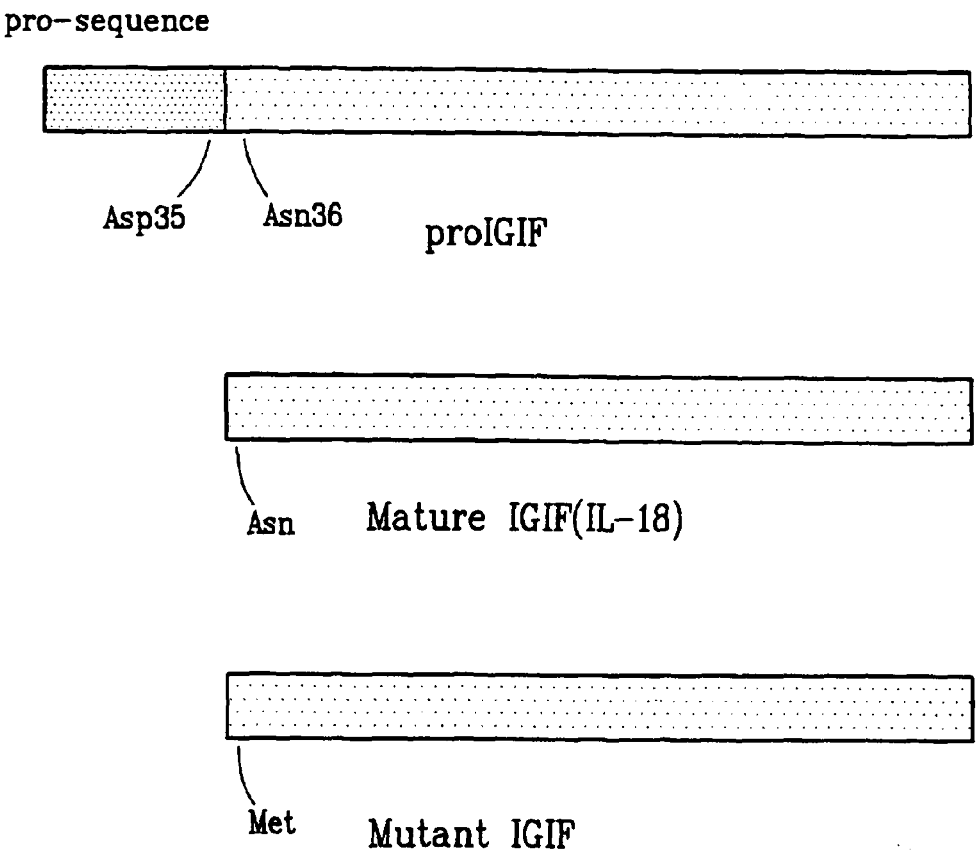

When the nucleotide sequence encoding IL-18 is delivered to certain cells as part of a vaccine or immunotherapeutic, it is less effect because it is inactive in full-length form and only becomes active when processed in mature form. As shown in FIG. 1A, the first 35 amino acids of IL-18 are cleaved by caspase-1 (ICE). A mutant IL-18 nucleotide sequence was constructed which is translated into the mutant IL-18 shown in FIG. 1B. This mutant form of IL-18 operates as an effective immunomodulating protein according to the invention. Delivery of nucleotide sequences that encode the mutant IL-18 in combination with nucleotide sequences that encode and immunogen result in an enhanced helper T cell response. The nucleotide sequence that encodes the mutant form may be inserted into pCDNA3.

Example 3

Delivery of nucleotide sequences that encode CD40 in combination with nucleotide sequences that encode and immunogen result in an enhanced CTL response.

Delivery of nucleotide sequences that encode CD40 in combination with ru nucleotide sequences that encode and immunogen result in an enhanced helper T cell response.

Delivery of nucleotide sequences that encode CD40L in combination with nucleotide sequences that encode and immunogen result in an enhanced CTL response.

Delivery of nucleotide sequences that encode Fas in combination with nucleotide sequences that encode and immunogen result in an enhanced CTL response.

Delivery of nucleotide sequences that encode ICAM-1 in combination with nucleotide sequences that encode and immunogen result in an enhanced CTL response.

Delivery of nucleotide sequences that encode ICAM-1 in combination with nucleotide sequences that encode and immunogen result in an enhanced helper T cell response.

Delivery of nucleotide sequences that encode LFA-3 in combination with nucleotide sequences that encode and immunogen result in an enhanced CTL response.

Delivery of nucleotide sequences that encode LFA-3 in combination with nucleotide sequences that encode and immunogen result in an enhanced helper T cell response.

Delivery of nucleotide sequences that encode VCAM-1 in combination with nucleotide sequences that encode and immunogen result in an enhanced helper T cell response.

Delivery of nucleotide sequences that encode PECAM-1 in combination with nucleotide sequences that encode and immunogen result in an enhanced helper T cell response.

Delivery of nucleotide sequences that encode E-selectin in combination with nucleotide sequences that encode and immunogen result in an enhanced helper T cell response.

Delivery of nucleotide sequences that encode MC-SF in combination with nucleotide sequences that encode and immunogen result in an enhanced CTL response.

Delivery of nucleotide sequences that encode GC-SF in combination with nucleotide sequences that encode and immunogen result in an enhanced CTL response.

Delivery of nucleotide sequences that encode M-CSF in combination with nucleotide sequences that encode and immunogen result in an enhanced helper T cell response.

Delivery of nucleotide sequentes that encode G-CSF in combination with nucleotide sequences that encode and immunogen result in an enhanced helper T cell response.

Delivery of nucleotide sequences that encode IL-4 in combination with nucleotide sequences that encode and immunogen result in an enhanced helper T cell response.

Delivery of nucleotide sequences that encode E-selectin in combination with nucleotide sequences that encode and immunogen result in an enhanced helper T cell response.

Delivery of nucleotide sequences that encode IL-7 in combination with nucleotide sequences that encode and immunogen result in an enhanced CTL response.

Delivery of nucleotide sequences that encode NGF in combination with nucleotide sequences that encode and immunogen result in an enhanced CTL response.

Delivery of nucleotide sequences that encode VEGF in combination with nucleotide sequences that encode and immunogen result in an enhanced CTL response.

Delivery of nucleotide sequences that encode IL-7 in combination with nucleotide sequences that encode and immunogen result in an enhanced helper T cell response.

Delivery of nucleotide sequences that encode NGF in combination with nucleotide sequences that encode and immunogen result in an enhanced helper T cell response.

Delivery of nucleotide sequences that encode VEGF in combination with nucleotide sequences that encode and immunogen result in an enhanced helper T cell response.

Delivery of nucleotide sequences that encode MCP-1 in combination with nucleotide sequences that encode and immunogen result in an enhanced CTL response.

Delivery of nucleotide sequences that encode RANTES in combination with nucleotide sequences that encode and immunogen result in an enhanced CTL response.

Delivery of nucleotide sequences that encode MCP-1 in combination with nucleotide sequences that encode and immunogen result in an enhanced helper T cell response. Delivery of nucleotide sequences that encode RANTES in combination with nucleotide sequences that encode and immunogen result in an enhanced helper T cell response.

Delivery of nucleotide sequences that encode MIP-1α in combination with nucleotide sequences that encode and immunogen result in an enhanced helper T cell response. Delivery of nucleotide sequences that encode IL-8 in combination with nucleotide sequences that encode and immunogen result in an enhanced helper T cell response.

Delivery of any one of MCP-1, RANTES, MIP-1α and IL-8 in combination with nucleotide sequences that encode and immunogen result in an enhanced antibody response.

Delivery of any one of MCP-1 or RANTES results in enhanced TNF-α production.

Delivery of any one of MCP-1, RANTES, MIP-1α and IL-8 in combination with nucleotide sequences that encode and immunogen result in enhanced IFN-γ production.

Example 4

We examined the effects on the antigen-specific immune responses following the co-delivery of the gene expression cassettes for M-CSF (macrophage-colony stimulating factor), G-CSF (Granulocyte-CSF), and GM-CSF (Granulocyte/Monocyte-CSF) along with HIV-1 DNA immunogen constructs. The genes for these cytokines were individually cloned into expression vectors under control of a cytomegalovirus (CMV) promoter. The gene plasmid expression cassettes were then injected into mice along with DNA vaccine cassettes for HIV-1 immunogens. We analyzed the immunological effects of the co-injection with these genetic adjuvant cassettes on the direction and magnitude of antigen-specific immune responses; these results were compared with the results we observed with co-delivery of genes for prototypical Th1 and Th2-type cytokines (IL-12 and IL-4, respectively). Using these DNA vaccine constructs as model antigens, we observed that CSF genes can dramatically and distinctly regulate antigen specific immune responses in vivo, and drive β-chemokine production in a vaccine-specific fashion.

Materials and Methods

DNA Plasmids

DNA vaccine constructs expressing HIV-1 envelope protein (pCEnv) and gag/pol protein (pCGag/Pol) were prepared as described in Boyer, J. D., et al. (1997) *Nature Med.* 3, 526-532, which is incorporated herein by reference. The genes for human G-CSF and M-CSF as well as murine GM-CSF were cloned into the pCDNA3 expression vector (Invitrogen, Inc., San Diego, Calif.) as described in Kim, J. J., et al. (1998) *Eur. J. Immunol.* 28, 1089-1103 and Kim, J. J., et al. (1998) *J. Clin. Invest.* 102, 1112-1124, which are incorporated herein by reference. Human G-CSF and M-CSF have been reported to be active in mouse cells. Clean plasmid DNA was produced in bacteria and purified using Qiagen Maxi Prep kits (Qiagen, Santa Clara, Calif.).

Reagents and Cell Lines

Mouse mastocytoma P815 cell lines were obtained from ATCC (Rockville, Md.). Recombinant vaccinia expressing HIV-1 envelope (vMN462), gag/pol (vVK1), and β-galactosidase (vSC8) were obtained from the NIH AIDS Research and Reference Reagent Program. Recombinant gp120 or p24 protein were obtained from ImmunoDiagnostics, Inc. (Bedford, Mass.).

DNA Inoculation of Mice

The quadriceps muscles of 6 to 8 weeks old female BALB/c mice (Harlan Sprague Dawley, Inc., Indianapolis, Ind.) were injected with 50 μg of each DNA construct of interest formulated in phosphate buffered saline (PBS) and 0.25% bupivacaine-HCl (Sigma, St. Louis, Mo.). Co-administration of various gene expression cassettes involved mixing the chosen plasmids prior to injection. The control mice were immunized with 50 μg of pCDNA3 vector. Each set of studies was performed three times and a representative set of results is presented. Mice received two DNA immunization (50 mg each) separated by two weeks. At one week after the boost injection, the mice were sacrificed, the spleens were harvested, and the lymphocytes were isolated and tested for cellular (Th or CTL) responses. All animals were housed in a temperature-controlled, light-cycled facility at the University of Pennsylvania, and their care was under the guidelines of the National Institute of Health and the University of Pennsylvania.

ELISA

Fifty μl of p24 or gp120 protein diluted in 0.1M carbonate-bicarbonate buffer (pH 9.5) to 2 mg/ml concentration was adsorbed onto microtiter wells overnight at 4° C. The plate were washed with PBS-0.05% Tween-20 and blocked with 3% BSA in PBS with 0.05% Tween-20 for one hour at 37° C. Mouse antisera was diluted with 0.05% Tween-20 and incubated for one hour at 37° C., then incubated with HRP-conjugated goat anti-mouse IgG (Sigma, St. Louis, Mo.). The plates were washed and developed with 3'3'5'5' TMB (Sigma) buffer solution. For the determination of relative levels of gp120-specific IgG subclasses, anti-murine IgG1 and IgG2a conjugated with HRP (Zymed, San Francisco, Calif.) was substituted for anti-murine IgG-HRP. This was followed by addition of the ABTS substrate solution (Chemicon, Temecula, Calif.). In each step, plates were washed 3 times with the wash buffer (PBS+0.05% Tween-X). The plates were read on a Dynatech MR5000 plate reader with the optical density at 450 nm.

T Helper Cell Proliferation Assay

Lymphocytes were harvested from spleens and prepared as the effector cells by removing the erythrocytes and by washing several times with fresh media. The isolated cell suspensions were resuspended to a concentration of $5\times10^6$ cells/ml. A 100 μl aliquot containing $5\times10^5$ cells was immediately added to each well of a 96 well microtiter flat bottom plate. Recombinant p24 or gp120 protein at the final concentration of 5 μg/ml and 1 μg/ml was added to wells in triplicate. The cells were incubated at 37° C. in 5% CO, for three days. One mCi of tritiated thymidine was added to each well and the cells were incubated for 12 to 18 hours at 37° C. The plate was harvested and the amount of incorporated tritiated thymidine was measured in a Beta Plate reader (Wallac, Turku, Finland). Stimulation Index was determined from the formula:

Stimulation Index (SI)=(experimental count/spontaneous count)

Spontaneous count wells include 10% fetal calf serum which serves as irrelevant protein control.

Cytotoxic T Lymphocyte Assay

A five hour $^{51}Cr$ release CTL assay was performed using vaccinia infected targets. The assay was performed with in vitro effector stimulation, where the effectors were stimulated with relevant vaccinia-infected cells (vMN462 for envelope and vVK1 for gag/pol) which were fixed with 0.1% glutaraldehyde for five days in CTL culture media at $5\times10^{6}$ cells/ml. The effectors were stimulated non-specifically for two days with CTL culture media consisting of RPMI 1640 (Gibco-BRL, Grand Island, N.Y.), 10% fetal calf serum (Gibco-BRL) and 10% RAT-T-STIM without Con A (Becton Dickinson Labware, Bedford, Mass.). Vaccinia infected targets were prepared by infecting $3\times10^{6}$ $^{P}$815 cells at the multiplicity of infection (MOI) of 10-20 for five to twelve hours at 37° C. A standard Chromium release assay was performed in which the target cells were labeled with 100 mCi/ml $Na_2{}^{51}CrO_2$ for 60 to 120 minutes and used to incubate with the stimulated effector splenocytes for four to six hours at 37° C. CTL lysis was determined at effector:target (E:T) ratios ranging from 50:1 to 12.5:1. Supernatants were harvested and counted on a LKB CliniGamma gamma-counter. Percent specific lysis was determined from the formula:

$$100\times\frac{\text{experimental release} - \text{spontaneous release}}{\text{maximum release} - \text{spontaneous release}}$$

Maximum release was determined by lysis of target cells in 1% Triton X-100 containing medium. An assay was not considered valid if the value for the 'spontaneous release' counts is in excess of 20% of the 'maximum release'.

Complement Lysis of CD8+ T Cells $CD8^{+}$ T cells were removed from the splenocytes by a treatment with α-CD8 monoclonal antibody (Pharmingen, San Diego, Calif.) followed by incubation with rabbit complement (Sigma) for 45 min. at 37° C.

Cytokine/Chemokine Expression Analysis

Supernatants from effectors stimulated for CTL assay were collected at day 6 and tested for cytokine and chemokine profiles using ELISA kits for IFN-γ and IL-4 (Biosource International, Inc., Camarillo, Calif.), and MIP-1α (R&D Systems, Minneapolis; MN), MIP-1β, and RANTES (Intergen, Pace, N.Y.).

Results

Construction of Cytokine Expression Cassettes

The cytokine genes were individually cloned into pCDNA3 plasmid expression vectors. To test whether the cytokine constructs expressed their relevant proteins, we transfected them in vitro into RD muscle cell line, and the expression of these constructs were analyzed by cytokine ELISA. Results demonstrate that each expression cassettes produced specific cytokines (G-CSF ~40-60 pg/ml; GM-CSF>70 pg/ml; M-CSF ~60-70 pg/ml).

G-CSF Induces Enhancement of T Helper Response

G-CSF is a growth factor produced by macrophages, fibroblasts, endothelial cells, and bone marrow stromal cells. G-CSF activates neutrophils, endothelial cells, and platelets, but is thought to have little direct effects on antigen presenting cells. We examined the effects of G-CSF co-expression on antigen specific antibody responses. Antisera from pCEnv and pCEnv+G-CSF immunized mice were collected and analyzed for specific antibody responses against HIV-1 gp120 protein by ELISA. The gp120-specific antibody titer from sera collected at 6 weeks post-DNA immunization was measured. G-CSF co-immunization did not significantly affect the level of gp120-specific antibody response. A similar result was observed with the groups immunized with pCGag/pol. Furthermore, the subclasses of gp120-specific IgGs induced by the co-administration with G-CSF genes were determined. It has been reported that production of IgG1 type is induced by Th2 type cytokines, whereas the IgG2a type production is induced by Th1 type cytokines. The relative ratios of IgG2a to IgG1 (Th1 to Th2) were measured. The pCEnv immunized group had a IgG2a to IgG1 ratio of 0.8. On the other hand, co-immunization of prototypical Th1 cytokine IL-12 genes increased the ratio to 1.28 and while co-injection with Th2 cytokine IL-4 gene resulted in a reduction of the ratio to 0.68. Co-administration with G-CSF increased the relative ratio to 1.1, indicating a shift to Th1-type response.

The effect of G-CSF co-expression on T helper cell proliferative response was also examined. T helper lymphocytes play a critical role in inducing both a humoral immune response via B cells and cellular immune response via $CD8^{+}$ cytotoxic T cells. Co-immunization of IL-12 genes dramatically enhanced the level of antigen-specific Th proliferative responses. In contrast, co-injection with IL-4 gene had minimal effects on the Th proliferative responses. G-CSF co-expression with HIV-1 immunogens resulted in positive enhancement of antigen-specific T helper cell proliferative responses.

In addition, the effects of cytokine co-expression on CTL response were also investigated. A background level of specific killing was observed from the control animals, whereas the animals immunized with pCEnv or pCGag/pol showed a small, but positive level of antigen-specific CTL responses. Co-injection with IL-12 genes dramatically enhanced the level of antigen-specific CTL responses. In contrast, co-immunization with IL-4 genes had minimal effects on the responses. Similarly, G-CSF co-administration did not have any enhancement effect on antigen-specific CTL responses.

Cytokines play a key role in directing and targeting immune cells during immune response. For instance, IFN-γ is intricately involved in the regulation of T cell-mediated cytotoxic immune responses while IL-4 plays a dominant role in B cell-mediated immune responses. We analyzed supernatant from the effector cells stimulated in vitro for CTL assay and tested them for the release of cytokines IFN-γ and IL-4. We found that G-CSF expression increased the level of IFN-g (2-fold), but it did not affect the level of IL-4 production.

GM-CSF is a Potent Inducer of Both Antibody and T Helper Responses

GM-CSF activates and differentiates granulocytic cells and can serve as growth factor for endothelial cells, erythroid cells, megakaryocytes, and T helper cells. It is unclear if GM-CSF can have effects on killer T cells. In contrast to G-CSF co-expression, GM-CSF co-expression had a significant enhancement effect (highest in all groups) in the induction of antigen-specific humoral response. Similar to IL-4 co-injection, GM-CSF co-immunization resulted in the highest level of envelope-specific antibody response. A similar result was seen with the groups immunized with pCGag/pol. On the other hand, pCEnv+GM-CSF co-immunization did not have any effect on the IgG2a/IgG1 ratio when compared to the group immunized with pCEnv alone. Furthermore, along with IL-12 co-immunization, GM-CSF co-expression with HIV-1 immunogens (pCEnv or pCGag/pol) resulted in the highest level of antigen-specific T helper cell proliferative responses. We also found that GM-CSF expression increased the level of IFN-γ (2-fold), but it did not affect the level of IL-4 production. In contrast, GM-CSF co-immunization had only slight effect on the antigen-specific CTL response.

M-CSF is a Potent Inducer of CTL Response

M-CSF is a potent activator of macrophages as well as macrophage progenitor cells. The M-CSF receptor has a restricted expression pattern, again limited to macrophages. As such the direct effects of M-CSF co-delivery on this APC population can be evaluated. Unlike GM-CSF, co-expression of M-CSF with pCEnv had positive enhancement effect (but less than IL-4 or GM-CSF) on the HIV-1 envelope-specific antibody response. The relative ratios of IgG2a to IgG1 following the co-administration with pCEnv+M-CSF were determined. The pCEnv immunized group had a IgG2a to IgG1 ratio of 0.8. On the other hand, co-injection with pCEnv+M-CSF increased the relative ratio to 1.2, indicating a strong shift to Th1-type response. Furthermore, M-CSF co-expression with HIV-1 immunogens (pCEnv or pCGag/pol) resulted in significant augmentation of antigen-specific T helper cell proliferative responses. Unlike co-injection with pCEnv+G-CSF or pCEnv+GM-CSF which resulted in a minimal effect in CTL activity, a more dramatic increase in the specific killing of targets infected with vaccinia (vMN462) expressing HIV-1 envelope was observed after co-injection with pCEnv+M-CSF. Almost 40% specific lysis of target cells was observed after co-injection with pCEnv+M-CSF at a 50:1 effector to target (E:T) ratio. Similarly, the mice immunized with pCGag/pol+M-CSF resulted in a significant enhancement of antigen-specific CTL lysis of targets infected with vaccinia (vVK1) expressing HIV-1 gag/pol. The level of IFN-γ release by mice immunized with pCEnv+M-CSF was significantly greater than those of the pCEnv immunized or the control groups. On the other hand, the level of IL-4 from these groups were similar.

Enhancement of CTL Responses by M-CSF Co-Immunization is CD8 T Cell-Restricted

To determine whether the increase in CTL response via co-expression of M-CSF was restricted to $CD8^+$ T cells, CTL assays were performed using a HIV-1 envelope peptide (RIHIGPGRAFYTTKN) which has been shown to be a specific epitope for MHC class I-restricted CTL for balb/c mice. Mice received two immunizations of 50 μg of each DNA construct separated by two weeks and their spleens were harvested one week after the second immunization. The CTL assay was performed on isolated splenocytes following in vitro stimulation with envelope-specific peptides as described. We observed a significant enhancement of CTL response after both co-injection with M-CSF at 40% specific killing at an E:T ratio of 50:1. We verified this observation by measuring CTL activity after the removal of CD8+ T cells from the effector cell population by complement lysis. The removal of $CD8^+$ T cells resulted in the suppression of antigen-specific CTL enhancement observed after co-injections with M-CSF. These results indicate that the enhancement of cytolytic activity was antigen-specific, class I-restricted and $CD8^+$ T cell dependent.

Co-Delivery of M-CSF Genes Modulate β-Chemokine Production by Stimulated T Cells We examined the expression profiles of β-chemokines (MIP-1α, MIP-1β, and RANTES) from stimulated T cells. These β-chemokines are the major HIV suppressive factors produced by $CD8^+$ T cells for macrophage-tropic, but not T cell tropic, viruses. Moreover, these $CD8^+$ T cell-produced chemokines have been shown play a critical role in cellular immune expansion in the periphery. Specifically, we observed that DNA immunization with pCEnv induces the β-chemokines MIP-1α, MIP-1β, and RANTES. Furthermore, we observed that co-immunization with hematopoietic cytokine genes resulted in increased expression of chemokines by the stimulated T cells. For instance, we observed that MIP-1α expression could be enhanced dramatically by co-immunization with pCEnv+G-CSF over the level expressed by pCEnv immunization alone. In addition, we found that MIP-1β expression was dramatically enhanced by pCEnv+M-CSF co-immunization. On the other hand, pCEnv+M-CSF, pCEnv+G-CSF, and pCEnv+GM-CSF co-immunizations did not result in significant enhancement of RANTES expression by stimulated effector cells over that induced by the DNA vaccine cassettes alone. Interestingly, however, M-CSF appears to down-modulate MIP-1α levels even lower than these induced by gene immunization on its own. This data could suggest that MIP-1α is not directly involved in driving a CTL response and may actually interfere with its induction.

Discussion

The manipulation of the local immune environment, possibly in the periphery of regional lymph node at the injected site or in the muscle, may influence both the magnitude and direction of the immune response. We examined the immune effects derived from co-delivering genes for G-CSF, GM-CSF, and M-CSF as molecular adjuvants for DNA vaccines.

We observed that G-CSF, GM-CSF, and M-CSF cDNA constructs all modulated DNA vaccine's immune profile uniquely. G-CSF is a pleiotropic cytokine best known for its specific effects on the proliferation, differentiation, and activation of hematopoietic cells of the neutrophilic granulocyte lineage. It is produced mainly by monocytes and macrophages upon activation by a variety of stimuli including, endotoxins, IL-1, TNF-α, and IFN-γ. It regulates proliferation and maturation of neutrophilic granulocyte precursors and acts directly on mature neutrophils to enhance phagocytosis, ADCC, superoxide generation, chemotaxis, and expression of cell-surface adhesion molecules. In vitro administration of G-CSF can stimulate neutrophilic colony formation from bone marrow hematopoietic progenitor cells. Clinically, G-CSF is most commonly administered for the treatment of chemotherapy and radiation therapy-induced neutropenia. We found that G-CSF co-immunization had minimal effect overall on antibody responses. G-CSF co-expression modulated the shift of immune responses to TM-type, indicated by the increase of IgG2a/IgG1 ratio and enhanced expression of IFN-γ. Moreover, G-CSF co-expression resulted in a moderate enhancement of T helper proliferative responses. Overall G-CSF, which should not directly affect antigen presentation, had at best a moderate effect on antigen specific immune responses.

GM-CSF is a pleiotropic cytolcine that can stimulate the proliferation, maturation, and function of a variety of hematopoietic cells. GM-CSF was first recognized for its ability to stimulate neutrophil, monocyte/macrophage, and eosinophil colony formation. It is produced by a variety of cell types, including T cells, B cells, macrophages, mast cells, endothelial cells, and fibroblasts, in response to cytokine or immune and inflammatory stimuli. We observed that GM-CSF was a strong inducer of CD4+ Th cells, indicated by strong T helper proliferative responses as well as strong boosting of antibody responses. On the other hand, pCEnv+GM-CSF co-immunization did not have any effect on the IgG2a/IgG1 ratio. In addition, GM-CSF co-administration did not seem to have noticeable effect on $CD8^+$ T cells, demonstrated by lack of any effects on the induction of antigen-specific CTL responses. Thus, vaccine help driven by this cytokine was entirely focused on the T helper cell. These results support and extend the previous studies on the use of GM-CSF cDNA constructs as a molecular adjuvant. It has been reported that intramuscular co-inoculation of plasmid expressing rabies virus glycoprotein and plasmid encoding mouse GM-CSF enhanced the B and T helper cell activity. Similarly, we reported that co-immunization of GM-CSF cDNA with DNA vaccine constructs increases antigen-specific antibody and Th-cell proliferation responses. In contrast, almost no effect on CTL induction was observed with the genes for GM-CSF in these studies. A similar finding was reported using GM-CSF co-delivery with DNA immunogen encoding for influenza nucleoprotein (NP). We also co-delivered GM-CSF cDNA constructs with DNA expression construct encoding for HSV-2 gD protein. We then analyzed the vaccine modulatory effects on resulting immune phenotype and on the mortality and the morbidity of the immunized animals following HSV lethal challenge. We observed that GM-CSF gene co-administration not only enhanced survival rate, but also reduced the frequency and severity of herpetic lesions following intravaginal HSV challenge.

M-CSF has been shown to be the regulator of the growth, differentiation and function of mononuclear phagocytes. It also increases the expression of adhesion molecules and Fc receptors, increases tumoricidal activity, enhances secondary release of cytokines including IL-1, TNF-α, and IFN-γ. M-CSF was originally discovered in serum, urine and other biological fluids as a factor that could stimulate the formation of macrophage colonies from bone marrow hematopoietic progenitor cells. M-CSF can be produced by a number of cells, including fibroblasts, secretory epithelial cells of the endometrium, bone marrow stromal cells, brain astrocytes, osteoblasts, renal mesangial cells, keratinocytes and LPS or cytokine-activated macrophages, B cells, T cells and endothelial cells. Among the CSFs examined, M-CSF was the most potent activator of $CD8^+$ CTLs. The enhancement of CTL responses induced by M-CSF expression was both MHC class I-restricted and $CD8^+$ T cell dependent. The enhanced CTL results are supported by increased production of IFN-γ and the increased IgG2a/IgG1 ratio. Unlike the effects of GM-CSF, M-CSF co-immunization had weak effect on antibody responses. Similar to the effects of GM-CSF, M-CSF co-expression with HIV-1 immunogens resulted in augmentation of antigen-specific T helper cell proliferative responses, although to a lesser degree. It appears that the CTL pathway is particularly benefitted by this cytokine.

It was interesting to compare the immunomodulatory effects of Th1/Th2-type cytokine and CSF genes. For instance, GM-CSF co-injection positively modulated the level of antibody responses similar to IL-4 co-immunization. On the other hand, the IL-4 co-immunization led to a more Th2-type response as seen by dramatic reduction in IgG2a/IgG1 ratio. Furthermore, the dramatic enhancement effect of GM-CSF co-injection on the Th proliferative responses was only matched by that of IL-12 co-administration. On the other hand, co-delivery of gene for M-CSF, and not G-CSF or GM-CSF, resulted in a significant enhancement of $CD8^+$ T cell-restricted CTL responses. These results indicate that the production of these growth factors at the site of immune activation could regulate the level of DNA vaccine-induced immune responses in vivo. Moreover, these results imply that these growth factors could play a more active role in modulating immune response cascade, which have been previously thought to be under the domain of traditional Th1 and Th2-type cytokines.

In addition to the analysis of the cell-based responses, we also examined the modulation of chemokine production resulting from the co-expression of CSF genes. Chemokines are important modulators of immune and inflammatory responses. They are especially important in the molecular regulation of trafficking of leukocytes from the vessels to the peripheral sites of host defense. Moreover, some chemokines have been shown play a critical role in the regulation on immune expansion in the periphery. We observed that $CD8^+$ effector T cells elevated chemokine expression levels while they primed immune responses suggests a regulatory role for these end-stage effector cells in the expansion phase of an antigen-specific immune response. In addition to their functions in inflammatory and immune responses, some chemokines may play a critical role in the transmission and progression of AIDS. It has been anticipated for over a decade that binding of HTV envelope glycoprotein gp120 to CD4 is not sufficient for viral fusion and entry, suggesting the requirement for an additional cell-surface cofactor for HIV infection. Recent studies have identified that the co-receptors required for the fusion of the T cell-tropic and macrophage-tropic HIV strains with their target cells to be CXCR-4 and CCR-5, respectively. The β-chemokines MIP-1α, MIP-1β, and RANTES are natural ligands for CCR-5 and are among the major HIV suppressive factors produced by $CD8^+$ T cells for macrophage-tropic, but not T cell tropic, HIV isolates.

We examined the expression of MIP-1α, MIP-1β, and RANTES by in vivo vaccine stimulated cells and observed that co-immunization with CSF genes resulted in increased expression of chemokines by antigen stimulated T cells. We observed that MIP-1α production could be dramatically enhanced by co-immunization with pCEnv+G-CSF over the level produced by pCEnv immunization alone. In particular, we found that MIP-1β expression was dramatically enhanced by pCEnv+M-CSF co-immunization. In contrast, none of the co-injection strategies resulted in significant enhancement of RANTES expression by stimulated effector cells. One other novel effect observed was the dramatic rise in RANTES and MIP-1β and at the same time, the decline in MIP-1α. In fact, MIP-1α levels induced by M-CSF were actually lower than control levels. This data suggests that MIP-1α signaling through CCR1, CCR4, and CCR5 results in a different signals than that delivered by RANTES or MIP-1β through either CCR3 or CCR9. This finding might distinguish these putative receptor effects on the immune responses.

These results show that co-delivery of the growth factor cDNA constructs modulate both humoral and cellular (including the production of chemokines) immune responses. In particular, co-injection with M-CSF had most modulatory effect on antigen-specific CTL induction and chemokine production.

Example 5

ICAM-1 Provides T Cell Costimulation and Chemokine Production

We examined the immunomodulatory effects of three specific adhesion molecules which are closely regulated by chemokines. We utilized DNA vaccine technology to explore the role of ICAM-1, LFA-3, and VCAM-1 in immune activation in vivo. Specifically, we cloned genes for ICAM-1, LFA-3, and VCAM-1 individually into expression vectors under control of a cytomegalovirus (CMV) promoter. These constructs were then co-immunized along with DNA immunogens encoding for HIV-1 envelope or gag/pol antigens. We analyzed the immunological effects of the co-injection with these adhesion molecule cassettes on the level of antigen-specific immune responses.

We observed that antigen-specific T cells responses can be enhanced by the co-expression of DNA immunogen and adhesion molecules ICAM-1 and LFA-3. However, ICAM-1 and LFA-3 appeared to play no role in expression of antigen-specific humoral responses. Rather, they appeared to specifically affect T cells responses. LFA-3 enhanced $CD4^+$ T cell responses and exhibited more minor effect on $CD8^+$ T cell function. More importantly, ICAM-1 co-administration dramatically increased both $CD4^+$ and $CM8^+$ T cell responses. ICAM-1 co-expression also dramatically enhanced antigen-specific β-chemokine production suggesting an important role for ligation of LFA-1 in peripheral T cell expansion. The activation phenotype of these molecules appeared to be distinct from the prototypic CD80/CD86 costimulatory molecules. These results support that the peripheral network of cytokine, chemokine, and adhesion molecules coordinately regulate effector T cell responses at the site of effector function.

Materials And Methods

DNA Plasmids

DNA vaccine constructs expressing HIV-1 envelope protein (pCEnv) and gag/pol protein (pCGag/Pol) were prepared as described in Kim, J. J., et al *Nature Biot.* 15:641-645, which is incorporated herein by reference. The genes for ICAM-1, LFA-3, and VCAM-1 were cloned into the pCDNA3 expression vector (Invitrogen, Inc., San Diego, Calif.) and clean plasmid DNA was produced as described in Kim, J. J., et al. *Eur. J. Immunol.* 28:1089-1103.

Reagents and Cell Lines

Human rhabdomyosarcoma (RD) and mouse mastocytoma P815 cell lines were obtained from ATCC (Rockville, Md.). Recombinant vaccinia expressing HIV-1 envelope (vMN462), gag/pol (vVK1), and β-galactosidase (vSC8) were obtained from the NIH AIDS Research and Reference Reagent Program. Recombinant gp120 or p24 protein were obtained from ImmunoDiagnostics, Inc. (Bedford, Mass.).

Expression of Adhesion Molecule Expression Constructs

Expression of ICAM-1, LFA-3, VCAM-1 constructs were analyzed by transfecting them into RD cells. Cells were harvested 72 hours after transfection and tested for expression using FACS analysis with fluorescein isothiocyanate (FITC)-conjugated monoclonal antibodies for ICAM-1, LFA-3, VCAM-1 (Pharmingen, San Diego, Calif.).

DNA Inoculation of Mice

The quadriceps muscles of 6 to 8 weeks old female BALB/c mice (Harlan Sprague Dawley, Inc., Indianapolis, Ind.) were injected with 50 μg of each DNA construct of interest formulated in phosphate buffered saline (PBS) and 0.25% bupivacaine-HCl (Sigma, St. Louis, Mo.). Co-administration of various gene expression cassettes involved mixing the chosen plasmids prior to injection. The control mice were immunized with 50 μg of pCDNA3 vector. Each set of studies was performed three times and a representative set of results is presented. Mice received two DNA immunization (50 μg each) separated by two weeks. At one week after the boost injection, the mice were sacrificed, the spleens were harvested, and the lymphocytes were isolated and tested for cellular (Th or CT L (cytotoxic T lymphocyte)) responses.

ELISA

Fifty μg of p24 or gp120 protein diluted in 0.1M carbonate-bicarbonate buffer (pH 9.5) to 2 μg/ml concentration was adsorbed onto microtiter wells overnight at 4° C. The plate were washed with PBS-0.05% Tween-20 and blocked with 3% BSA in PBS with 0.05% Tween-20 for one hour at 37° C. Mouse antisera was diluted with 0.05% Tween-20 and incubated for one hour at 37° C., then incubated with HRP-conjugated goat anti-mouse IgG (Sigma, St. Louis, Mo.). The plates were washed and developed with 3'3'5'5' TMB (Sigma) buffer solution. The plates were read on a Dynatech MR5000 plate reader with the optical density at 450 nm.

T Helper Cell Proliferation Assay

Lymphocytes were harvested from spleens and prepared as the effector cells by removing the erythrocytes and by washing several times with fresh media. The isolated cell suspensions were resuspended to a concentration of $5\times10^6$ cells/ml. A 100 ml aliquot containing $5\times10^5$ cells was immediately added to each well of a 96 well microtiter flat bottom plate. Recombinant p24 or gp120 protein at the final concentration of 5 μg/ml and 1 μg/ml was added to wells in triplicate. The cells were incubated at 37° C. in 5% $CO_2$ for three days. One mCi of tritiated thymidine was added to each well and the cells were incubated for 12 to 18 hours at 37° C. The plate was harvested and the amount of incorporated tritiated thymidine was measured in a Beta Plate reader (Wallac, Turku, Finland). Stimulation Index was determined from the formula:

Stimulation Index (SI)=(experimental count/spontaneous count)

Spontaneous count wells include 10% fetal calf serum which serves as an irrelevant protein control. In addition, pCEnv or control immunized animals routinely have SI of 1 against Pr55 protein. Similarly, pCGag/pol or control routinely have SI of 1 against gp120 protein. To assure that cells were healthy, PHA or con A (Sigma) was used as a polyclonal stimulator positive control. The PHA or con A control samples had a SI of 20-40.

Cytotoxic T Lymphocyte Assay

A five hour $^{51}Cr$ release CTL assay was performed using vaccinia infected targets. The assay was performed with in vitro effector stimulation, where the effectors were stimulated with relevant vaccinia-infected cells (vMN462 for envelope and vVK1 for gag/pol) which were fixed with 0.1% glutaraldehyde for five days in CTL culture media at $5\times10^6$ cells per ml. The effectors were stimulated non-specifically for two days with CTL culture media consisting of RPMI 1640 (Gibco-BRL, Grand Island, N.Y.), 10% fetal calf serum (Gibco-BRL) and 10% RAT-T-STIM without Con A (Becton Dickinson Labware, Bedford, Mass.). Vaccinia infected targets were prepared by infecting $3\times10^6$ P815 cells at the multiplicity of infection (MOI) of 10-20 for five to twelve hours at 37° C. A standard Chromium release assay was performed in which the target cells were labeled with 100 mCi/ml $Na_2{}^{51}CrO_4$ for 60 to 120 minutes and used to incubate with the stimulated effector splenocytes for four to six hours at 37° C. CTL lysis was determined at effector:target (E:T) ratios ranging from 50:1 to 12.5:1. Supernatants were harvested and counted on a LKB CliniGanuna gamma-counter. Percent specific lysis was determined from the formula:

$$100\times\frac{\text{experimental release}-\text{spontaneous release}}{\text{maximum release}-\text{spontaneous release}}$$

Maximum release was determined by lysis of target cells in 1% Triton X-100 containing medium. An assay was not considered valid if the value for the 'spontaneous release' counts is in excess of 20% of the 'maximum release'.

Complement Lysis of CD8+ T cells $CD8^+$ T cells were removed from the splenocytes by a treatment with α-CD8 monoclonal antibody (Phanningen, San Diego, Calif.) followed by incubation with rabbit complement (Sigma) for 45 min. at 37° C.

Cytokine and Chemokine Expression Analysis

Supernatants from effectors stimulated for CTL assay were collected at day 6 and tested for expression using ELISA kits for IFN-γ and IL-4 and for MIP-1α, MIP-1β, and RANTES (Biosource, Camarillo, Calif.; R&D Systems, Minneapolis, Minn.; Intergen, Purchase, N.Y.).

Results

ICAM-1, LFA-3, and VCAM-1 Can be Expressed by Transfected Cells

Figure 2:
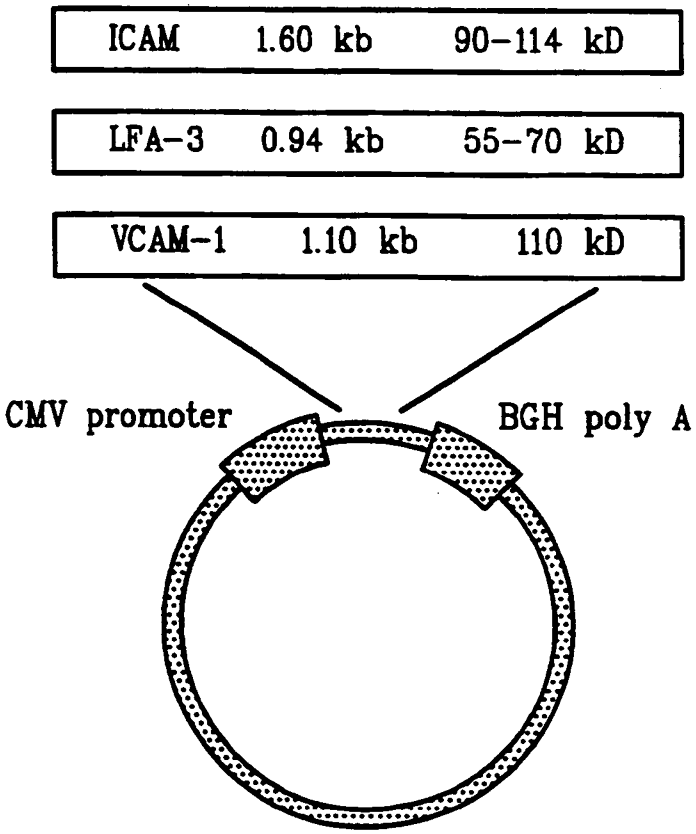
FIG. 2 shows the genes for ICAM-1 (pCICAM-1), LFA-3 (pCLFA-3), and VCAM-1 (pCVCAM-1) cloned into the pCDNA3 expression vector.

The genes for ICAM-1 (pCICAM-1), LFA-3 (pCLFA-3), and VCAM-1 (pCVCAM-1) were individually cloned into the pCDNA3 expression vector (FIG. 2). To test whether pCICAM-1, pCLFA-3, and pCVCAM-1 constructs could express their relevant proteins, we transfected them in vitro into the human rhabdomyosarcoma (RD) cells. Using FACS analysis we observed that transfection of pCICAM-1, pCLFA-3, and pCVCAM-1 expression cassettes resulted in specific expression of ICAM-1, LFA-3, and VCAM-1, respectively. We also observed that co-immunization of two DNA expression cassettes intramuscularly resulted in co-expression of both encoded proteins in same muscle cells in vivo.

Co-Expression of Adhesion Molecules does not Affect Ag-Specific Humoral Immune Responses We next investigated the effects the co-expression of adhesion molecules have on the induction of antigen-specific immune responses. For all experiments, 50 μg of each DNA expression constructs were injected into BALB/c mice intramuscularly at weeks 0 and 2. The first immune parameter examined was the antigen-specific humoral response. Antisera from immunized mice were collected at weeks 0, 2 and 6 and were analyzed for specific antibody responses against HIV-1 gp120 protein by ELISA. Co-expression of ICAM-1, LFA-3, or VCAM-1 appeared to have a minimal effect on the specific antibody binding profile induced by pCEnv immunization. A similar result was seen with the groups co-immunized with pCGag/pol.

Co-Expression of ICAM-1 or LFA-3 Enhances Ag-Specific Th Proliferative Responses The effect of adhesion molecule co-expression on the magnitude of cellular immune responses were also investigated. Induction of $CD4^+$ T helper cell proliferative response is important because Th cells play a critical role in inducing both a humoral immune response via B cells and CTL response via $CD8^+$ T cells. The Th proliferative responses for the mice immunized with pCGag/pol and those mice co-immunized with pCICAM-1, pCLFA-3, or pCVCAM-1 were measured. Recombinant gp120 HIV-1 envelope protein (5 μg/ml and 1 μg/ml) was plated in each well for specific stimulation of T cell proliferation. We also analyzed these groups for non-specific stimulation of T-cells using irrelevant proteins and observed that nonspecific antigen did not induce T-cell proliferative responses in vitro. A background level of proliferation was observed in the control group immunized with a control vector, and a moderate level of proliferation was observed in the group immunized with pCEnv alone. In contrast, the groups co-immunized with either pCICAM-1 or pCLFA-3 had significantly higher levels of proliferative responses. On the other hand, the group co-immunized with VCAM-1 genes did not show any enhancement of antigen-specific Th response. A similar result was seen with the groups co-immunized with pCGag/pol. In repeat experiments using either immunogens, co-delivery of pCICAM-1 or pCLFA-3 resulted in a 3 to 4 fold increase in antigen-specific proliferative responses.

Co-Expression of ICAM-1 or LFA-3 Enhances Ag-Specific CTL Responses

To further investigate the enhancement of cellular immunity, we performed CTL assays using splenocytes of mice co-immunized with pCEnv and pCGag/pol. The assay was performed with in vitro stimulation of effector splenocytes prior to measuring chromium release from specific and non-specific vaccinia infected or peptide treated targets. To calculate specific lysis of targets, the percent lysis of irrelevant targets was subtracted from the percent lysis of specific targets. A background level of specific ru killing was observed from the control animals with pCDNA3, pCICAM-1, pCLFA-3, or pCVCAM-1 immunizations, while the animals immunized with pCEnv showed low level of CTL response. On the other hand, co-immunization with pCEnv+pCICAM-1 resulted in a dramatic increase in CTL activity. Greater than 40% specific killing of HIV-1 envelope vaccinia (vMN462) infected targets was observed after co-immunization with pCEnv+pCICAM-1 at a 50:1 effector to target (E:T) ratio. The CTL activity titered out to 20% specific lysis at a 12.5:1 E:T ratio. In contrast, co-immunization with pCEnv+pCLFA-3 resulted in a more moderate increase in CTL activity. Similar CTL results were observed following co-immunizations with pCGag/pol+pCICAM-1 and pCGag/pol+pCLFA-3.

To determine whether the increases in CTL response via co-expression of pCICAM-1 and pCLFA-3 were restricted to $CD8^+$ T cells, CTL assays were performed by measuring CTL activity with and without the removal of $CD8^+$ T cells from the effector cell population by complement lysis. The removal of $CD8^+$ T cells resulted in the suppression of antigen-specific CTL enhancement observed after co-injections with pCICAM-1 and pCLFA-3. These results indicate that the enhancement of cytolytic activity was antigen-specific and $CD8^+$ T cell dependent.

Co-Expression of ICAM-1 or LFA-3 Increases Production of IFN-γ by Stimulated T Cells Analysis of cytokine production by stimulated CTLs in the immunized animals support the CTL results observed. Cytokines play a key role in directing and targeting immune cells during the development of the immune response. For instance, IFN-γ is intricately involved in the regulation of T cell-mediated cytotoxic immune responses while IL-4 plays a dominant role in B cell-mediated immune responses. We analyzed supernatant from the effector cells stimulated in vitro for CTL assay and tested them for the release of cytokines IFN-γ and IL-4. We found that co-injection with pCICAM-1 increased the level of IFN-γ significantly. Co-immunization with pCLFA-3 resulted in a more moderate increase in IFN-γ production. On the other hand, the level of IL-4 released from all groups were similar.

Co-Expression of ICAM-1 Dramatically Increases Production of β-Chemokines by Stimulated T Cells Recently we reported that $CD8^+$ effector T cells expand antigen-specific responses in vivo through the production of specific chemokines at the peripheral site of infection. Therefore, we analyzed the production of β-chemokines by stimulated CTLs. We analyzed supernatant from the effector cells stimulated in vitro for CTL assay and tested them for the release of β-chemokines MIP-1α, MIP-1β, and RANTES. As we had previously observed, we found that DNA immunization with pCEnv induced significantly greater levels of expression of MIP-1α, MIP-1β, and RANTES over those of control vector. Moreover, we observed that co-injection with pCEnv+pCLFA-3 increased the level of β-chemokine production over that of the pCEnv immunized group. Even more significantly, co-immunization with pCEnv+pCICAM-1 resulted in a dramatic enhancement (2-4 fold) of MIP-1α, MIP-1β, and RANTES production over that of the pCEnv immunized group. In contrast, co-administration of pCVCAM-1 did not enhance the level of chemokine expression. These results support that ICAM-1 and LFA-3 provide direct T cell costimulation.

Co-Expression of ICAM-1 and CD86 Synergistically Enhances Ag-Specific CTL Responses The B7 (CD80 and CD86) pathway is considered to be a major costimulatory pathway for the delivery of critical second signals to prime and expand T cell responses. These molecules have been examined in the context of DNA vaccines as modulatory agent. In this context, it appears that CD86 molecules play a prominent role in the antigen-specific induction of $CD8^+$ cytotoxic T lymphocytes when delivered as vaccine adjuvants. Co-administration of CD86 cDNA along with DNA immunogens dramatically increased antigen-specific $CD8^+$ CTL response. The effects of ICAM-1 and LFA-3 could be dependent on B7-CD28 signals, or they could represent an alternative synergistic pathway for driving CTL induction in vivo. Therefore, we further investigated whether ICAM-1 and LFA-3 molecules when co-expressed with CD86 molecule could synergistically enhance the level of CTL induction. We observed that co-expression of ICAM-1 and CD86 molecules could synergistically enhance antigen-specific CTL response. On the other hand, co-expression of LFA-3 and CD86 molecules did not improve the level of CTL response. These results indicate that ICAM-1/LFA-1 pathways provide T cell costimulatory signals independent of CD86/CD28 pathways, and they may work synergistically to expand T cell responses in vivo.

The level of IFN-γ and β-chemokines MIP-1α, MIP-1β, and RANTES production by stimulated CTLs further support these results indicating that ICAM-1/LFA-1 signals work independent of CD86/CD28 signals and work concordantly to expand T cell responses. When we analyzed supernatant from the effector T cells using the methods described above, we observed that co-administration of LFA-3 and CD86 genes resulted in a dramatically higher level of IFN-γ, MIP-1α, MIP-1β, and RANTES. These results further imply the synergistic nature of ICAM-1 and CD86 in T cell activation.

Discussion

During immune or inflammatory response, lymphocytes traffic to the site of antigen exposure. Adhesion molecules on lymphocytes and endothelial cells play an important role in providing direct cellular contact and directing the migration of the leukocytes. In addition, adhesion molecules play an important role in the binding of T lymphocytes to APCs. ICAM-1 (CD54) is a 90-114 kD molecule which is expressed on endothelial cells, macrophages, and dendritic cells, and binds to LFA-1 and Mac-1. Almost all leukocytes, including T lymphocytes express LFA-1, whereas Mac-1 expression is more restricted to monocytes, macrophages, and granulocytes. LFA-3 (CD58) is a 55-70 kD surface molecule expressed by various cell types including the APCs (Springer, T. A., et al. 1987 *Ann. Rev. Immunol.* 5:223-252, which is incorporated herein by reference). Vascular cell adhesion molecule-1 (VCAM-1) is a 110 kD surface molecule which is expressed on activated endothelial cell and smooth muscle cells (Osborn, L., et al. 1989. *Cell.* 59:1203-1211 which is incorporated herein by reference). VCAM-1 recognizes and binds to very late antigen-4 (VLA-4) which is constitutively expressed on most mononuclear leukocytes, including the eosinophils, lymphocytes, monocytes, and basophils, but is absent on neutophils (Elices, M. J., et al. 1990 *Cell.* 60:577-584, which is incorporated herein by reference). VCAM-1/VLA-4 interaction plays an important role in leukocyte migration and diapedesis.

In this study, we utilized a DNA immunogen model to investigate the roles of these cell surface adhesion molecules in providing stimulatory signals required for T cell activation and expansion. In a two signal T cell activation model, the primary activation signal is mediated by the ligation of antigenic peptide-MHC complexes to T cell receptor. The secondary costimulatory signal is provided through the ligation of CD80/CD86 costimulatory molecules with their receptors (CD28/CTLA-4) present on T cells. Although this two-signal model is conceptually straight-forward and well supported by experimental results, the costimulatory signals provided during T cell activation process may not be restricted only to the B7 (CD80/CD86) molecules. Additional cell surface molecules such as the adhesion molecules on the APCs may also have an important function in providing costimulation, and their roles in providing direct signals to $CD4^+$ and $CD8^+$ T cells are under investigation.

Adhesion molecules are important in leukocyte trafficking, inflammatory cell recruitment, and immune surveillance. Recently, a role for adhesion molecules in T cell activation has been suggested. We investigated the role using a subset of adhesion molecules which all bind to ligands on T cells. We chose three related molecules ICAM-1 (CD54), LFA-3 (CD58), and VCAM-1 (CD106). Utilizing DNA expression cassettes encoding for ICAM-1, LFA-3, and VCAM-1 along with our DNA immunogens, we sought to identify the specific effects of co-expressing adhesion molecules along with antigens. We observed that antigen-specific T cell (both $CD4^+$ and $CD8^+$ T cells) responses can be enhanced by the co-expression of DNA immunogen and adhesion molecules ICAM-1 and LFA-3. Co-expression of ICAM-1 or LFA-3 molecules along with DNA immunogens resulted in a significant enhancement of Th cell proliferative responses. In addition, co-immunization with pCICAM-1 (and more moderately with pCLFA-3) resulted in a dramatic enhancement of CD8-restricted CTL responses. These observations were further supported by the finding that co-injection with LFA-3 increased the production level of IFN-γ as well as β-chemokines MIP-1α, MIP-1β, and RANTES by stimulated $CD8^+$ T cells. More impressively, co-immunization with ICAM-1 resulted in a more dramatic enhancement of IFN-γ and β-chemokines. It is also important to note that increased cellular contact or juxtaposition of cells alone was not enough to enhance antigen-specific T cell-mediated responses. Even though ICAM-1 and VCAM-1 have similar molecular sizes, the co-injection with VCAM-1 did not have any measurable effect on T cell responses. On the other hand, ICAM-1 co-expression dramatically enhanced the level of both CD4+ and CD8+ T cell responses. These results imply that the T cell stimulatory effects are not inherent to their adhesion properties or the size of the molecules. It is interesting that both CTL driving adhesion molecules which enhanced CTLs (ICAM-1 and LFA-3) are expressed on a variety of APCs. In fact, it may be important that the best CTL inducing adhesion molecule, ICAM-1, is expressed on dendritic cells.

We also compared the enhanced induction of CTLs with that enhanced with CD86 expression. We observed that combining the expression of CD86 molecules with ICAM-1, but not LFA-3 molecules could enhance antigen-specific CTL responses. These results were further supported by significantly enhanced production of IFN-γ as well as β-chemokines MIP-1α, MIP-1β, and RANTES which play important role in immune activation in the periphery. Even though the elucidation of the biological significance of these molecules requires further studies, a recent study found a relationship between chemokines MIP-1β and RANTES and CTL response. Although additional studies could provide more insight into the costimulatory role of these molecules, these results indicate that ICAM-1 molecules can provide T cell costimulatory signals through an independent pathway to CD86, and they may work synergistically to amplify the total level of costimulatory signals provided to T cells. Overall, these results support that adhesion molecules. ICAM-1 and LFA-3 can provide important costimulatory signals, indicating that the simple two-signal model of T cell activation, although conceptually useful, may be incomplete, and a newer model with multiple sources of costimulation should be further considered and studied. These results also indicate that further studies aimed at utilizing the T cell costimulatory function of other cell surface molecules are warranted.

One important issue with regard to these studies is exactly where are these molecules functioning to enhance the cellular immune response. Recent studies have reported that injection of plasmid DNA can, with low efficiency, transfect resident APC's including macrophages and dendritic cells. These results are further supported by studies using bone-marrow chimeras which illustrate the requirement for bone-marrow derived cells to prime DNA immune responses. It is consistent with the literature that some costimulation observed in our study can occur through transfection and enhanced T cell priming by resident professional APC's.

Along with previous reports, these results support the role for ICAM-1 and LFA-3 in T cell costimulation. It appears that LFA-3 has particular effects on Class II responses while in general, ICAM-1 was a climatically strong driver of CTL induction and $CD8^+$ effector function as demonstrated by enhanced production of β-chemokines. These results also support a concordant hypothesis for the recruitment and expansion of T cell effectors in the periphery. We recently reported that in addition to their chemoattractant functions, chemokines regulate modulation and expansion of antigen-specific immune responses at the peripheral site. We observed that CD8+ T effector cells control chemokine expression levels while they primed immune responses. Thus, in chemotaxis, chemokines regulate the movement of lymphocytes through a concentration gradient. Moreover, commensurate redistribution of adhesion molecule expression provide direct cell-to-cell contact in directing the lymphocytes to the periphery. In addition, expression of adhesion molecules are modulated by various inflammatory cytokines and chemokines. For instance, IFN-γ and TNF-α have been shown to upregulate ICAM-1 expression on endothelial and muscle cells.

$CD8^+$ effector T cells therefore elaborate chemokines which would recruit more APCs and T cells to the site of inflammation. These T cells would be stimulated by β-chemokine production to enhance expression of adhesion molecules which could serve to drive IFN-γ production and allow for T cell costimulation. Thus, once at the site of inflammation, these effector CTLs can be further regulated through the expression of specific chemokines and adhesion molecules which would expand the level of effector function. These results further support that end-stage effector T cells in the expansion phase of an antigen-specific immune response could direct their destiny through coordinated expression and release of these molecules.

Example 6

Adhesion and Costimulatory Molecules Induce Distinct Antigen-Specific Immune Responses and Enhance Protective Immunity Against Herpes Simplex Virus-2 In Vivo CD40 ligand and leukocyte function associated proteins (LFA) on T cells interact with CD40 and intercellular adhesion molecules (ICAM) on APC, respectively. We coimmunized with costimulatory molecules CD40 and CD40 ligand, and adhesion molecules LFA-3 and ICAM-1, and then analyzed immune modulatory effects on a gD plasmid vaccine and on protection against lethal challenge with HSV-2. We observed that systemic gD-specific IgG production was significantly enhanced by coinjection with LFA-3. However, little change in IgG production was observed by coinjection with CD40, CD40 ligand and ICAM-1. Furthermore, Th1 type cellular responses were driven by CD40 ligand, whereas both Th1 and Th2 type immune responses were driven by LFA-3. Codelivery with CD40 ligand and LFA-3 also enhanced survival rate from lethal HSV-2 challenge. These studies demonstrate that costimulatory and adhesion molecules have distinct costimulatory pathways and that they can play an important role in generating protective antigen-specific immunity.

The specific roles of costimulatory and adhesion molecules in the induction of antigen-specific immune responses were tested as well as vaccine effect of using costimulatory and adhesion molecule as part of plasmid delivery to drive DNA vaccine induced protective immunity in a mouse HSV-2 challenge model system. We observed that costimulatory and adhesion molecules differentially modulate antigen-specific immune responses. In particular, co-delivery with costimulatory molecule, CD40 ligand and adhesion molecule, LFA-3 induced significant $CD4^+$ T cell activities in an antigen dependent manner and enhanced survival from lethal HSV-2 challenge.

Materials and Methods

Mice—Female 4- to 6-week-old BALB/c mice were purchased from Harlan Sprague-Dawley (Indianapolis, Ind.). They were cared for under the guidelines of the National Institutes of Health (Bethesda, Md.) and the University of Pennsylvania 1ACUC (Philadelphia, Pa.).

Reagents—HSV-2 strain 186 (a kind gift from P. Schaffer, University of Pennsylvania, Philadelphia, Pa.) was propagated in the Vero cell line (American Type Culture Collection, Rockville, Md.). Recombinant HSV-2 gD proteins were used as recombinant antigens in these studies. Human rhabdomyosarcoma (RD) cell line was obtained from ATCC (Rockville, Md.).

Plasmids and DNA Preparation—The DNA vaccine, pAPL-gD2 encoding HSV-2 gD protein was prepared as described in Pachuk, et al. 1998 Current topics Microbiol. Immunol. 226, 79, which is incorporated herein by reference. The cDNA for CD40, CD40 Ligand, LFA-3 and ICAM-1 were cloned into the expression vector pCDNA3 to produce pCDNA3-CD40, pCDNA3-CD40 Ligand, pCDNA3-LFA and pCDNA3-ICAM-1, respectively. Plasmid DNA was produced in bacteria and purified by double banded CsCl preparations.

In vitro expression of CD40 and CD40 ligand gene constructs—Expression of CD40, CD40 Ligand, LFA-3, and ICAM-1 constructs were analyzed by transfecting them into RD cells. Cells were harvested 72 hours after transfection and tested for expression using FACS analysis with fluorescein isothiocyanate (FITC)-conjugated monoclonal antibodies for LFA-3, ICAM-1, CD40 and CD40 Ligand (Pharmingen, San Diego, Calif.).

DNA inoculation of mice—The quadriceps muscles of BALB/c mice were injected with gD DNA constructs formulated in 100 μl of phosphate-buffered saline and 0.25% bupivacaine-HCl (Sigma, St. Louis, Mo.) via a 28-gauge needle (Becton Dickinson, Franklin Lakes, N.J.). Samples of various chemokine and cytokine gene expression cassettes were mixed with pgD plasmid solution prior to injection.

ELISA—Enzyme-linked immunosorbent assay (ELISA) was performed to determine the relative levels of gD-specific IgG subclasses using anti-murine IgG1 and IgG2a conjugated with HRP (Zymed, San Francisco, Calif.). The ELISA titers were determined as the reverse of the highest sera dilution showing the same optical density as sera of naive mice.

Chemokines, Th1 and Th2 type cytokines—A 1 ml aliquot containing $6\times10^6$ splenocytes was added to wells of 24 well plates. Then, 1 μg of HSV-2 gD protein/ml was added to each well. After 2 days incubation at 37° C. in 5% $CO_2$, cell supernatants were secured and then used for detecting levels of IL-2, IL-10, IFN-γ, RANTES, MCP-1, and MIP-1α using commercial cytokine kits (Biosource, Intl., Camarillo, Calif. and R&D Systems, Minneapolis, Md.) by adding the extracellular fluids to the cytokine or chemokine-specific ELISA plates.

Intravaginal HSV-2 challenge—Before inoculating the virus, the intravaginal area was swabbed with a cotton tipped applicator (Hardwood Products Company, Guiford, Me.) soaked with 0.1 M NaOH solution and then cleaned with dried cotton applicators. Mice were then examined daily to evaluate survival rates.

Statistical analysis—Statistical analysis was done using the paired Student's t test and ANOVA. Values between different immunization groups were compared. p values<0.05 were considered significant.

Results

CD40, CD40 ligand, LFA-3, and ICAM-1 can be expressed by transfected cells—The genes for CD40, CD40 ligand, LFA-3, and ICAM-1 were individually cloned into the pCDNA3 expression vector. To test whether CD40, CD40 ligand, LFA-3 and ICAM-1 constructs could express their relevant proteins, we transfected them in vitro into the human RD cells. Using FACS analysis we observed that transfection of CD40, CD40 ligand, LFA-3, and ICAM-1 expression cassettes resulted in specific expression of CD40, CD40 ligand, LFA-3 and ICAM-1, respectively. RD cells were transfected with pCDNA3 (control) or pCDNA3 expressing CD40, CD40 Ligand, LFA-3 and ICAM-1. Three days following transfection the cells were removed from the plates and were analyzed by FACS analysis using α-CD40, α-CD40 ligand, α-LFA-3, α-ICAM-1 antibodies to detect expression of the transfected gene product.

LFA-3 enhances systemic IgG response—To determine if coinjection of gD genetic vaccines with CD40, CD40 ligand, LFA-3 and ICAM-1 expression vectors might influence systemic IgG responses against gD, one hundred dilution of sera after the DNA inoculation was tested in ELISA. Each group of mice (n=8) was immunized twice with gD DNA vaccines (60 μg) plus costimulatory molecule genes (40 μg). Mice were bled 2 weeks after the second DNA injection and then sera were diluted to 1:100 for reaction with gD. Coinjection with gD DNA vaccine (60 μg per mouse) plus CD40 or CD40 ligand plasmid DNAs (40 μg per mouse) had no significant effect on overall IgG levels. Equally pooled sera per group were serially diluted to determine ELISA titer. ELISA titers of equally pooled 2 week post second immunization were also determined as 6,400 (CD40), 6,400 (CD40 ligand), and 6,400 (gD DNA vaccine alone). The similar result was also observed when we tested sera obtained 1 month after coinjecting once with gD DNA vaccine (10 μg per mouse) plus these costimulatory molecules (40 μg per mouse).

Groups of mice (n=8) were immunized with gD DNA vaccines (60 μg) plus LFA-3 adhesion molecule genes (40 μg) at 0 and 2 weeks. Mice were bled bi-weekly and then sera were diluted to 1:100 for reaction with gD. Coinjection with LFA-3 cDNA enhanced systemic IgG responses significantly higher than gD DNA vaccine alone while little change was observed by coinjecting ICAM-1 cDNA. Equally pooled sera per group were serially diluted to determine ELISA titer. Optical density was measured at 405 nm. Values and bars represent mean (n=8) and the standard deviation. The ELISA titers were determined to be the reverse of the highest dilution showing the same optical density as sera of naïve mice. ELISA titers of equally pooled 2 week post second immunization were also determined as 25,600 (LFA-3), 6,400 (ICAM-1), and 6,400 (gD DNA vaccine alone).

CD40 ligand and LFA-3 influence IgG isotype pattern. IgG subclasses give an indication of the Th1 vs Th2 nature of the induced immune responses. We analyzed the IgG subclasses induced by the coinjections with CD40, CD40 ligand, LFA-3 and ICAM.-1. Levels of gD-specific IgG isotypes in mice immunized with DNA vectors were measured. Each group of mice (n=8) was immunized twice with gD DNA vaccines (60 μg) plus either costimulatory molecule genes (40 μg) or adhesion molecule genes (40 (g). Mice were bled 2 weeks after the second DNA injection and then equally pooled sera per group were diluted to 1:100 for reaction with gD. Optical density was measured at 405 nm. Coinjection with CD40 ligand genes increased the relative production of gD-specific IgG2a to IgG1, whereas coinjection with CD40 genes showed the similar IgG isotype pattern to gD DNA vaccine alone. This shift in IgG production illustrates that a more Th1 type response is induced by coinjection with only CD40 ligand cDNA. However, coinjection with LFA-3 increased both IgG1 and IgG2a isotypes significantly higher than gD DNA vaccine alone or ICAM-1 coinjection. This increase indicates that both Th1 and Th2 type responses are induced by coinjection with LFA-3 cDNA CD40 ligand and LFA-3 enhance Tb cell proliferation responses—T helper cells play an important role in eliciting both humoral and cellular immune responses via expansion of Ag stimulated B cells and expansion of $CD8^+$ T cells, respectively. As a specific indicator of CD4 activation T cell proliferation was examined. It is important to measure proliferation levels of T cells obtained after coimmunization with cytokine genes when stimulated in vitro with a specific antigen. The gD-2 protein (1 and 5 μg/ml) was used for antigen specific stimulation of T cells. For a positive control, 5 μg/ml PHA was used as a polyclonal stimulator. A low background level of Th cell proliferation was observed in negative controls. However, gD DNA vaccination induced Th cell proliferation responses much higher than negative controls. When coinjected with CD40 ligand and LFA-3 cDNAs, Th cell proliferation levels were further boosted. However, little increase in Th cell responses was detected in animals coinjected with CD40 and ICAM-1 cDNAs. This tendency was observed over the two different gD antigen concentrations tested, reflecting that this effect is CD40 ligand and LFA-3-mediated. The gD plasmid vaccination does not result in CTL responses due to a lack of CTL epitope in the Balb/c background. However, to evaluate cellular effects in more detail we next examine cytokine production profiles.

CD40 ligand and LFA-3 influence production of Th1 and Th2 type cytokines. Th1 cytokines (IL-2 and IFN-γ) and Th2 cytokines (IL-4, IL-5 and IL-10) have been a mainstay in our understanding of the polarization of immune responses. Th1 immune responses are thought to drive induction of cellular immunity, whereas Th2 immune responses preferentially drive humoral immunity. Thus, we examined whether gD DNA vaccination with and without costimulatory molecules induces Th1 or Th2 immune responses. Production levels of IL-2, IL-10, IFN-γ, RANTES, MIP-1α and MCP-1 from splenocytes in mice coimmunized with either costimulatory molecules or adhesion molecules were measured. Each group of mice (n=2) was immunized with gD DNA vaccines (60 μg) plus either costimulatory molecule genes or adhesion molecule genes (40 μg) at 0 and 2 weeks. Two weeks after the last DNA injection, two mice were sacrificed and spleen cells were pooled. Splenocytes were stimulated with 1 μg/ml gD-2 proteins for 2 days. IL-2, and IFN-γ productions were significantly enhanced by coinjection with CD40 ligand cDNA while IL-10 production was reduced by this coinjection. However, coinjection with CD40 plus gD genes had slightly increasing effect on IFN-γ in this assay. However, IL-2, IL-10 and IFN-γ productions were all enhanced by coinjection with LFA-3 cDNA significantly higher than gD DNA vaccine, whereas coinjection with ICAM-1 plus gD genes had slightly increasing effect in this assay. This supports that CD40 ligand drives immune responses towards Th1 phenotype while LFA-3 influences both Th1 and Th2 immune phenotypes in vivo.

CD40 ligand and LFA-3 influence production of β chemokines—Beta chemokines (CC type) including RANTES (regulated on activation, normal T cell expressed and secreted), MIP (macrophage inflammatory protein)-1α, and MCP (monocyte chemotactic protein (MCP)-1 chemoattact particularly monocytic phagocytes, and activate T cells, basophils, eosinophils, and mononuclear phagocyte as well as a variety of other soluble immune modulators. As compared to MCP-1, RANTES and MIP-1α were also reported to be a major HIV suppressive factor. These molecules are thought to be important in modulating inflammatory immune responses. However, their direct role in infectious diseases is under investigation. The relationship of CD40, CD40 ligand, LFA-3 and ICAM-1 molecules as a vaccine adjuvant to chemokine production in vivo is unknown. We investigated the levels of chemokines (RANTES, MCP-1, and MIP-1α) induced by coinjection with gD DNA vaccine plus CD40 ligand, CD40, LFA-3 and ICAM-1 cDNAs. gD DNA vaccine alone enhanced production of RANTES, MCP-1 and MIP-1α in an antigen specific manner. Furthermore, coinjection with CD40 ligand cDNA enhanced RANTES and MIP-1α production significantly higher than gD DNA vaccine alone. In contrast, MCP-1 production was unaffected by CD40 ligand coinjection. However, coinjection with CD40 molecules showed slightly increasing effect on the β(chemokine production. Data showed that coinjection with LFA-3 cDNA enhanced RANTES and MIP-1α production significantly higher than gD DNA vaccine alone. Similarly, production of RANTES and MIP-1α was enhanced by ICAM-1 coinjection. In contrast, MCP-1 production was inhibited by ICAM-1 coinjection. This modulation supports that costimulatory and adhesion molecules can have specific effects on production of individual members of the β chemokine family.

CD40 ligand and LFA-3 enhance protection from intravaginal (i.vag.) HSV challenge. A lethal dose $(LD)_{50}$ of HSV-2 (186) was previously measured. To determine if using CD40, CD40 ligand, LFA-3 and ICAM-1 cDNAs as a molecular adjuvant in gD genetic vaccination could influence protection from HSV-2 challenge, mice were immunized with both DNA vaccines and the individual costimulatory and adhesion molecule cDNAs, and then challenged i.vag. with 4 $LD_{50}$ of HSV-2. Intravaginal infection route was chosen as HSV-2 infects mucocutaneously and causes urogenital infections. Survival rates of mice immunized twice with gD DNA vaccines plus costimulatory or adhesion molecule genes were measured. Each group of mice (n=10) was immunized once with gD DNA vaccines (10 μg) plus costimulatory or adhesion molecule genes (40 μg). Four weeks after the DNA immunization, mice were challenged i.vag. with 4 $LD_{50}$ of HSV-2 strain 186 ($1.4\times10^4$ pfu). When mice were immunized with gD DNA vaccine, 60% of survival was noted, but all naive mice died within 13 days following viral challenge. However, coinjection with CD40 ligand increased survival rate to 100%, a 40% enhancement of protection rate, whereas coinjection with CD40 cDNA showed minimal protective effects, as compared to gD DNA vaccine alone. Furthermore, coinjection with LFA-3 cDNA increased survival of mice to 90%. However, coinjection with ICAM-1 cDNA showed slightly better effects on protection from HSV-2 infection.

Discussion

During antigen presentation, costimulatory molecules of APC are important for the initiation and differentiation of T cell responses. In particular, the CD40L-CD40 interaction induces B7 and IL-12 expression from APC. IL-12 also enhances CD40 ligand expression from T cells, whereas IFN-γ inhibits CD40 ligand expression, indicating that there might be an auto-regulatory mechanism for induction of CD40 ligand on T cells. Moreover, cytokines, IL-2 and IL-4 also enhance CD40 ligand expression on anti-CD3 stimulated T cells, indicating that there is a cooperative regulation between costimulatory molecules and cytokines in mediating immune responses in vivo. Furthermore, the CD40-CD40 ligand interaction increases Th cell-dependent antibody responses, proinflammatory cytokine production, and is required for macrophage tumoricidal and microbicidal activities. In particular, CD40 ligand is not expressed on resting T cells, but induced by CD3-TCR triggering processes. CD40 (45-to 50-kDa glycoprotein) is a member of the TNF receptor superfamily and is expressed on B cells, monocytes, and dendritic cells. However, its ligand, CD40 ligand (gp39) is a type II transmembrane protein with sequence homology to TNF-α and transiently expressed on activated T cells. However, interaction of adhesion molecule, LFA-3 on T cells with ICAM-1 on APC is highly regulated by conformation change of LFA-3 that with a high affinity and avidity for ICAM-1. It has been known that costimulation of LFA-3 in the context with CD3 monoclonal antibody or Class II plus antigen results in T cell proliferation and higher production of a variety of cytokines from T cells. Furthermore, interaction of LFA-3 with ICAM-1 triggers signal pathways. As compared to costimulatory CD40/CD40 ligand molecules, co-localization of these adhesion molecules and anti-CD3 or anti-TCR antibody on the surface is necessary for proper signaling to T cells.

Coinjecting APC-stimulating or attracting molecules along with DNA vaccines results in a more efficient induction of both arms of immunity. In intramuscular (i.m.) injection, DNA is taken up into myofibers with subsequent endogenous expression, leading to presentation of a natural form of antigen to the immune system. Secreted antigens are ingested by phagocytosis and then presented as a peptide-MHC II complex by macrophages which can provide the primary activation signal, costimulatory ligands and cytokines necessary for stimulation of naive T cells. Recent evidence also supports direct transfection of APC in vivo following either i.m. or skin delivery of DNA vaccines. Coinjection of DNA vaccines with costimulatory molecules, such as B7.1 and B7.2, dramatically enhanced antigen-specific cellular immune responses, such as Th cell proliferation responses and cytotoxic T cell activities. Similarly, coinjection with GM-CSF genes enhances both antibody and cellular immune responses in the viral DNA vaccine models. Coinjection with pLacZ plus CD40 ligand cDNAs enhances both humoral and cellular, in particular CTL in an antigen-dependent manner. However, there have been no HSV challenge studies via codelivery with costimulatory and adhesion molecules. It would be also interesting to compare these two different pathways in induction of antigen-specific immune responses and protective immunity against HSV-2.

We observed that no significant increase in gD-specific IgG production through vaccine modulation with the CD40 and CD40 ligand genes. However, this is not compatible with previous finding that coinjection with CD40 ligand enhanced antibody production to an antigen when delivered with DNA vector (β-galactosidase). This discrepancy might be due to the nature of the antigens tested. However, there is a similar finding in which the similar IgG isotype production pattern was induced by coinjection with CD40 ligand coinjection. In our studies, codelivery with CD40 ligand induced a significant increase in IgG2a production, as compared to IgG1 isotype which is believed of to be mediated by Th1 type immune responses. This implies that polarization of gD-specific immune responses to Th1 type is achieved by coinjecting plasmid vectors driving expression of CD40 ligand. In contrast, significant increase in gD-specific IgG production was observed by coinjection with LFA-3, as compared to gD DNA vaccine alone or ICAM-1 coinjection. This indicates that LFA-3 could enhance antibody responses in vivo. We also observed that LFA-3 coinjection enhanced production of both Th1 and Th2 isotypes indicated by increased production of IgG1 and IgG2a isotypes, implying that LFA-3 could drive both Th1 and Th2 immune responses in vivo.

Increased Th cell proliferation was achieved by coinjecting plasmid DNAs encoding CD40 ligand. This is again compatible with previous findings in other models that CD40 ligand molecules increase antigen-specific Th cell proliferation and IFN-γ production as well as CTL responses. This pattern is in line with the cytokine production levels we observed as coinjection with CD40 ligand cDNA enhanced both IL-2 and IFN-γ secretion, but inhibited IL-10 production. Thus, the use of the CD40 ligand cDNA in gD DNA vaccination was effective for polarizing the immune responses towards a Th1 phenotype, increasing cell-mediated immunity. However, coinjection with LFA-3 enhanced production of IL-2, IL-10 and IFN-γ while coinjection with ICAM-1 slightly enhanced the cytokine production. This supports the IgG isotype pattern that LFA-3 drives immune responses to both Th1 and Th2 phenotypes.

Chemokines have been recently reported to play an important role in a manner reminiscent of cytokines in the immune and inflammatory responses. Ocular inflammatory disease mediated by HSV infection was suppressed by topical administration of Th2 type cytokine protein (IL-10). This application resulted in suppressed chemokine production. The disease (inflammation in the eye) was also ameliorated by injection with anti-MIP-1α but not MCP-1, indicating that MIP-1α again segregates as a Th1 type chemokine. However, the role of chemokines on infectious status is under investigation. In this study, production of RANTES and MIP-1α was enhanced by codelivery of CD40 ligand higher than CD40, suggesting that CD40 ligand molecules play an important role in regulating β chemokine production from T cells. Both LFA-3 and ICAM-1 enhanced production of MIP-1α and RANTES. In contrast, MCP-1 production was unaffected by LFA-3 or inhibited by ICAM-1, indicating that adhesion molecules could also regulate β chemokine production in vivo.

It has been reported that humoral, cellular or both immune responses could be responsible for protective immunity against HSV infection. Passive immunization with HSV-specific monoclonal antibodies resulted in protection from lethal HSV infection. During viral infection, neutralizing antibodies can inactivate free viral particles, but are not able to inhibit intracellular HSV infection. It appears that antibody-dependent, complement-mediated and antibody-dependent cell-mediated cytotoxicity (ADCC) are insufficient to control HSV infection. Thus, it has been suggested that HSV-specific cellular-mediated immunity may play a major effector function to eradicate HSV-infected cells and control HSV infection. Importance of cellular immune responses mediated by $CD4^+$ and/or $CD8^+$ T cells on control of HSV infection has been well documented We observed that coinjection with CD40 ligand molecules induces significantly enhanced protection from mortality resulting from HSV-2 infection. This suggests that there is a positive correlation between protective immunity and Th1 type cellular immunity, which is supported by increased Th cell proliferation responses and IFN-γ production levels when coinjected with CD40 ligand molecules. Our observation is compatible with the previous finding that coinjection with CD40 ligand enhances protective immunity against challenge with *Leishmania major* or with metastatic tumor expressing antigen. We also observed that LFA-3 induces significantly enhanced protection from mortality resulting from HSV-2 infection. It seems that LFA-3 enhancement of cellular and/or humoral immunity is responsible for reducing HSV-2-derived mortality in this system. It is also possible that CD40 ligand or LFA-3-induced IFN-γ might be partially responsible for the anti-HSV-2 activity in vivo. Thus, CD40 ligand and LFA-3-driven cellular or humoral mediated immunity appears to be correlated with protection from HSV infection.

In conclusion, the data presented here suggest that costimulatory and adhesion molecules have different costimulatory pathways in the induction of antigen-specific immune responses. In particular, CD40 ligand drives immune responses to a Th1 type while LFA-3 favors both Th1 and Th2 immune types. Such activities have previously only been associated with cytokines. These data indicate that costimulatory molecules have as central role as cytokines in the induction of antigen-specific immunity. Also CD40 ligand and LFA-3 mediate enhanced protection against lethal HSV-2 challenge in gD DNA vaccination. This finding broadens our weapons for infectious diseases.

Example 7

We analyzed modulatory effects of chemokines (IL-8, IP-10, RANTES, MCP-1, MIP-1α) on immune phenotype and protection against lethal challenge with HSV-2. We observed that IL-8 and RANTES coinjection dramatically enhanced antigen-specific immune responses and protection from lethal HSV-2 challenge. However, coinjection with MCP-1 and IP-10 increased mortality of the challenged mice. These studies demonstrate that chemokines can dominate and drive immune responses in a manner more reminiscent of cytokines, playing an important role in the generation of protective antigen-specific immunity.

The initiation of immune or inflammatory reactions is a complex process involving the coordinated expression of costimulatory molecules, adhesion molecules, cytokines, and chemokines. In particular, chemokines are important in the molecular regulation of trafficking of immune cells to the peripheral sites of host defenses. The chemokine superfamily consists of two subfamilies based upon the presence (a family) or absence (β family) of a single amino acid sequence separating two cysteine residues α and β chemokines have been shown to induce direct migration of various immune cell types, including neutrophils, eosinophils, basophils, and monocytes. Recently, the (chemokine family (CXC type), interleukin (IL)-8 and interferon-γ inducible protein (IP)-10, and the β chemokine family (CC type), RANTES (regulated on activation, normal T cell expressed and secreted), monocyte chemotactic protein (MCP)-1 and macrophage inflammatory protein (MIP)-1α have been shown to chemoattract T lymphocytes. In particular, IL-8 and IP-10 have been known to chemoattract neutrophils, inducing them to leave the bloodstream and migrate into the surrounding tissues. Similarly, RANTES chemoattracts monocytes, stimulated $CD4^+$/$CD45RO^+$ memory T cells and stimulated $CD4^+$ and $CD8^+$ T cells. MIP-1α has been known to chemoattract and degranulate eosinophils. MIP-1α also induces histamine release from basophils and mast cells and chemoattacts basophils and B cells. MCP-1 is an important chemokine in chronic inflammatory disease. MCP-1 induces monocytes to migrate from the bloodstream to become tissue macrophages. MCP-1 also chemoattracts T lymphocytes of the activated memory subset. Recent studies support that chemokine receptors mark T cell subsets and that chemokines may be involved in the generation of antigen-specific immune responses.

To investigate the modulation of immune responses and protective immunity, we co-delivered a DNA expression construct encoding HSV-2 gD protein with plasmids encoding for chemokines (IL-8, IP-10, RANTES, MCP-1, MIP-1α). We then analyzed their modulatory effects in antigen-specific immune induction and protection from challenge. We first investigated the in vivo effects of selected chemokines on the induction of antigen-specific antibody responses. As controls we immunized animals with gD vaccine and 2 proinflammatory cytokines, TNF family genes (TNF-α and TNF-β). These proinflammatory cytokines were studied as they are thought to similarly be involved in early immune responses and should serve as positive controls. ELISA was used to measure levels of systemic gD-specific IgG in mice (Balb/c) immunized with DNA vectors. Each group of mice (n=10) was immunized with gD DNA vaccines (60 μg per mouse) plus chemokine genes (40 μg per mouse) or TNF genes (40 μg per mouse) at 0 and 2 weeks. DNA constructs expressing gD antigens and chemokines were previously cloned (Pachuk, et al. 1998 Current topics Microbiol. Immunol. 226, 79; Kim, et al. 1998 J. Clin. Invest. 102, 1112; and Kim, et al. 1998 Eur. J. Immunol. 28, 1089). The mice were bled 2 weeks after the second immunization, and then equally pooled sera per group were serially diluted for reaction with gD. The ELISA titers were determined as the reverse of the highest sera dilution showing the same optical density as sera of naive mice. The absorbance (O.D.) was measured at 405 nm. ELISA titers of equally pooled sera collected 2 weeks post the second immunization were determined as 12,800 for IL-8, 6,400 for IP-10, 6,400 for RANTES, 6,400 for MCP-1, 12,800 for MIP-1α. 25,600 for TNF-α, 6,400 for TNF-β and 6,400 for the gD DNA vaccine alone. This shows that coinjection with IL-8 and MIP-1α genes results in a moderate, but not significant enhancement of gD-specific IgG antibodies. In contrast, IP-10, RANTES or MCP-1 showed similar levels of antibody responses to that of pgD vaccination alone. The TNF-α cDNA control resulted in systemic IgG levels significantly higher than those of gD DNA vaccine alone.

It has been reported that induction of the IgG1 isotype is induced by Th2 type cytokines, whereas the IgG2a isotype production is influenced and driven in vivo by Th1 type cytokines. This has been used as an indicator for determining if immune responses are under control of Th1 or Th2 cytokines. We analyzed the IgG subclasses induced by the coinjections. IgG isotypes induced by each immunization group were measured. Each group of mice (n=10) was immunized with gD DNA vaccines (60 μg per mouse) plus chemokine genes (40 μg per mouse) or TNF genes (40 μg per mouse) at 0 and 2 weeks. The mice were bled 2 weeks after the last immunization and then sera were diluted to 1:100 for reaction with gD. For the determination of relative levels of gD-specific IgG subclasses, anti-murine IgG1, IgG2a, IgG2b, or IgG3 conjugated with HRP (Zymed, San Francisco, Calif.) were substituted for anti-murine IgG-HRP. The absorbance (O.D.) was measured at 405 nm. The relative optical density was calculated as optical density of each IgG subclass/total optical density. Line bars represent the mean (n=10) of relative optical densities of each mouse IgG subclass. The relative ratios of IgG2a to IgG1 (Th1 to Th2) were measured. The pgD immunized group had a IgG2a to IgG1 ratio of 0.62. Coinjection with IL-8, RANTES or TNF-α genes increased the relative ratio of gD-specific IgG2a to IgG1 to 0.8. On the other hand, coinjection with IP-10 and MIP-1α decreased the relative ratio of IgG2a to IgG1 (0.3 and 0.4), whereas co-immunization with MCP-1 or TNF-β genes resulted in an IgG subtype pattern similar to pgD vaccination alone. This analysis supports that IL-8 and RANTES drive immune responses towards Th1 phenotype in vivo in a similar manner to γ-IFN type cytokines. Thus, these results extend prior findings in the HIV model that the shift in humoral immune responses to either Th1 or Th2 could be modulated by chemokines, again suggesting that chemokines can modulate cytokine production in vivo.

Th cell proliferation is a standard parameter used to evaluate the potency of cell-mediated immunity. We measured Th cell proliferative responses following co-immunization with chemokine genes by stimulating splenocytes from immunized animals in vitro with gD proteins. Th-cell proliferation levels of splenocytes after in vitro gD stimulation in mice (Balb/c) coimmunized with a-chemokine cDNA, β-chemokine cDNA and the TNF controls. Each group of mice (n=2) was immunized with gD DNA vaccines (60 μg per mouse) plus chemokine genes (40 μg per mouse) or TNF genes (40 μg per mouse) at 0 and 2 weeks. Two weeks after the last DNA injection, two mice were sacrificed and spleen cells were pooled for the proliferation assay. Splenocytes were stimulated with 1 and 5 μg of gD-2 proteins per ml and 5 μg of PHA per ml as a positive control. After 3 days of stimulation, the cells were harvested and the cpm was counted. Samples were assayed in triplicate. The PHA control sample showed a stimulation index of 40-50. pgD DNA vaccination alone resulted in gD-specific Th cell proliferative responses. We also observed the significant enhancement of Th cell proliferative responses over that of gD DNA vaccine alone by co-injection with IL-8, RANTES and TNF-α cDNAs. We also observed a slight enhancement in proliferation by coinjection with TNF-β genes. In contrast, co-immunization with IP-10, MCP-1 and MIP-1α genes appeared to have minimal effects on the levels of Th cell proliferative responses. However, the coinjections showed no effects on PHA-induced non-specific Th cell proliferative responses (S.I. range was 40 to 50). The gD plasmid vaccination does not result in CTL responses due to a lack of CTL epitope in the Balb/c background. However, to evaluate cellular effects in more detail we next examine cytokine production profiles.

Th1 cytokines (IL-2 and IFN-γ) and Th2 cytokines (IL-4, IL-5 and IL-10) have been a mainstay in our understanding of the polarization of immune responses. Th1 immune responses are thought to drive induction of cellular immunity, whereas Th2 immune responses preferentially drive humoral immunity. Based on the IgG phenotype results we further evaluated the Th1 vs Th2 issue by analyzing directly cytokine release. As shown in Table 4, IL-2 production was dramatically increasedalmost 7 fold by coinjection with IL-8 cDNA. IL-2 was also induced by coinjection with TNF-α cDNA, and by coinjection with the MIP-1α cassette. In particular, production of IFN-γ was most significantly enhanced by codelivery of RANTES, 20 fold and IL-8, 6 fold, further supporting the isotyping results and demonstrating that IL-8 and RANTES mediate Th1 type cellular immune responses in an antigen-dependent fashion. RANTES, IL-8, TNF-α, and TNF-β coinjections also enhanced IL-10 production significantly higher than pgD vaccine alone. This illustrates that IL-8 and RANTES drive T cells of predominantly Th1 over a Th2 type.

To determine if chemokine coinjection could induce β chemokine production in an antigen-dependent manner, we coimmunized and then analyzed release levels of β chemokines of splenocytes after in vitro stimulation with recombinant gD antigen or control antigen. As shown in Table 5, MCP-1 production was dramatically increased by coinjection with IL-8 cDNA, but was decreased by coinjection with RANTES and MIP-1α cassettes. In particular, production of MIP-1α is most significantly enhanced by codelivery of RANTES and IL-8. In the case of RANTES, IL-8 and RANTES coinjections enhanced RANTES production higher than pgD vaccine alone. This indicates that RANTES modulates antigen-specific immune responses differently from IL-8 in the HSV model. This also supports that chemokines modulate their own production.

HSV is the causative agent of a spectrum of human diseases, such as cold sores, ocular infections, encephalitis, and genital infections. HSV can establish viral latency with frequent recurrences in the host. During viral infection, neutralizing antibody inactivates viral particles, but is unable to control intracellular HSV infection. Rather, cellular-mediated immunity plays a major effector function for eradication of HSV-infected cells and spread of HSV in vivo. Adoptive transfer of cytotoxic T lymphocyte (CTL) raised against HSV results in complete protection from lethal HSV challenge in animals. Furthermore, there have been several reports that Th1 type $CD4^+$ T cells play more crucial role for protection from HSV-2 challenge. When $CD4^-$ T cells were depleted in vivo, protective immunity against HSV was lost. Moreover, Th1 type $CD4^+$ T cells generate a large amount of IFN-γ. IFN-γ upregulates class I and II expression on HSV-infected cells to allow better recognition by cytotoxic $CD4^-$ T cells and CD8+ CTL, and has direct anti-HSV effects. Codelivery with Th1 type cytokine cDNAs enhanced survival from lethal HSV-2 challenge while codelivery with Th2 type cytokine cDNAs worsened the disease status. Similarly, protection enhanced by codelivering with a prototypic Th1 type cytokine IL-12 cDNA was mediated Th1 type $CD4^+$ T cells in HSV challenge model, underscoring the importance of Th1 type T cell-mediated protective immunity against HSV infection.

It is important that antigen-specific immune modulation influences pathogen replication. Survival rates of mice (Balb/c) immunized with gD DNA vaccines plus a chemokine cDNA, β chemokine cDNA and the TNF controls were measured. Each group of mice (n=8) was immunized with gD DNA vaccines (60 μg per mouse) plus chemokine genes (40 μg per mouse) or TNF genes (40 μg per mouse) at 0 and 2 weeks. Three weeks after the second immunization, the mice were challenged i.vag. with 200 $LD_{50}$ of HSV-2 strain 186 ($7\times10^5$ PFU). Before inoculating the virus, the intravaginal area was swabbed with a cotton tipped applicator (Hardwood Products Company, Guiford, Me.) soaked with 0.1 M NaOH solution and then cleaned with dried cotton applicators. Mice were then examined daily to evaluate survival rates. Surviving mice were counted for 61 days following viral challenge. This was repeated once with the expected results We analyzed protective efficacy of chemokine coinjection in the murine herpes challenge model. Mice were coimmunized i.m. with DNA vectors at 0 and 2 weeks and then challenged with HSV-2 at 3 weeks post second immunization. Intravaginal challenge route was chosen as HSV-2 infects mucocutaneously. Immunization with gD DNA vaccine alone resulted in 63% of survival of mice from intravaginal challenge with 200 $LD_{50}$ of HSV-2. Coinjection with IL-8 and RANTES cDNA increased the survival rate to 88%, an almost 30% enhancement of protection rate, whereas coinjection with MCP-1 and IP-10 decreased the survival rate to 25%, more than a 50% reduction in overall survival from the gD vaccine alone. Similarly, MIP-1α coinjection also negatively influenced the survival rate of vaccinated animals. These observations are striking if one considers the total number of animals tested in each chemokine group (survival rates of gD alone, 11 of 18, 61%; survival rates of IL-8, 17 of 18, 94%; survival rates of IP-10, 5 of 18, 28%; survival rates of RANTES, 17 of 18 94%; survival rates of MCP-1, 6 of 18, 33%; survival rates of MIP-1α, 8 of 18, 44%). This indicates that coinjection with IL-8 and RANTES chemokine gene enhances protection from lethal HSV challenge while coinjection with IP-10 and MCP-1 and to a less degree MIP-1α make animals more susceptible to viral infection in spite of the induction of immune responses. This supports that chemokines IL-8 and RANTES enhanced protection from HSV-2 infection through antigen-specific immune modulation. These studies support that chemokines can act and modulate important immune responses and disease progression in a manner reminiscent of cytokines (Th1 vs Th2). Significant immune modulation could be achieved through the use of codelivered chemokine cDNAs, impacting not just an immune responses but also disease protection. Furthermore, use of chemokine gene-delivered adjuvants, in particular IL-8 and RANTES could be important in crafting more efficacious vaccines or in immune therapies for HSV. We previously reported that coinjection with Th1 type cytokine gene enhances protection rate from lethal HSV challenge while Th2 type cytokine coinjection increases susceptibility of animal to viral infection. In pathogenesis studies, the importance of Th1-like cytokine response for resistance from pathogenic infection has been reported. Thus, it seems likely that Th1 and/or Th2 type immune responses are being driven by these chemokines, resulting in an impact on protection from HSV infectious challenge based on the quality of the immune responses.

We compared the protective efficacy of TNF family coinjection in the herpes challenge model. Coinjection with both TNF-α and TNF-β genes also reduced the rate of survival of challenged mice to 25%, more than 50% reduction in overall survival from the gD vaccine alone. Although gD-specific antibody and Th cell proliferation levels as well as cytokine production levels (IL-2, IFN-γ, IL-10) of mice co-injected with TNF-α genes were much higher than those of gD DNA vaccination alone, TNF cytokine-mediated susceptibility to HSV-2 infection was observed in those animals. The reason for this observation is unclear but strongly supports that the quality of the responses is significantly important for controlling pathogenic infection.

In conclusion, the data presented here demonstrate that chemokines could modulate immune responses to Th1 and/or Th2 types in an antigen-dependent fashion. Such activities have been previously only been associated with cytokines, implying that chemokines have as central a role as cytokines in the induction of antigen-specific immunity. The use of chemokines to modulate immune responses for immune therapies and vaccination is worthy of further investigation.

TABLE 1

| | |
|---|---|
| MadCAM-1 | |
| Accession: | U80016 |
| Authors: | Leung, E., et al. |
| Journal: | Immunogenetics 46 (2), 111-119 (1997) |
| MadCAM-1 | |
| Accession: | U43628 |
| Authors: | Shyjan, A. M., et al. |
| Journal: | J. Immunol. 156 (8), 2851-2857 (1996) |
| NGF | |
| Accession: | M57399 |
| Authors: | Kretschmer, P. J., et al. |
| Journal: | Growth Factors 5, 99-114 (1991) |
| IL-7 | |
| Accession: | J04156 |
| Authors: | Goodwin, R. G., et al. |
| Journal: | Proc. Natl. Acad. Sci. U.S.A. 86 (1), 302-306 (1989) |
| VEGF | |
| Accession: | M32977 |
| Authors: | Leung, D. W., et al. |
| Journal: | Science 246, 1306-1309 (1989) |
| TNF-R | |
| Accession: | M60275 |
| Authors: | Gray, P. W., et al. |
| Journal: | Proc. Natl. Acad. Sci. U.S.A. 87, 7380-7384 (1990) |
| TNF-R | |
| Accession: | M63121 |
| Authors: | Himmler, A., et al. |
| Journal: | DNA Cell Biol. 9, 705-715 (1990) |
| Fas | |
| Accession: | M67454 |
| Authors: | Itoh, N., et al. |
| Journal: | Cell 66 (2), 233-243 (1991) |
| CD40L | |
| Accession: | L07414 |
| Authors: | Gauchat, J. F. M., et al. |
| Journal: | FEBS Lett. 315, 259-266 (1992) |
| IL-4 | |
| Accession: | M23442 |
| Authors: | Arai, N., et al. |
| Journal: | J. Immunol. 142 (1), 274-282 (1989) |
| IL-4 | |
| Accession: | M13982 |
| Authors: | Yokota, T., et al. |
| Journal: | Proc. Natl. Acad. Sci. U.S.A. 83 (16), 5894-5898 (1986) |
| CSF | |
| Accession: | M37435 |
| Authors: | Wong, G. G., et al. |
| Journal: | Science 235 (4795), 1504-1508 (1987) |
| G-CSF | |
| Accession: | X03656 |
| Authors: | Nagata, S., et al. |
| Journal: | EMBO J. 5 (3), 575-581 (1986) |

TABLE 1-continued

| | |
|---|---|
| G-CSF | |
| Accession: | X03655 |
| Authors: | Nagata, S., et al. |
| Journal: | EMBO J. 5 (3), 575-581 (1986) |
| GM-CSF | |
| Accession: | M11220 |
| Authors: | Lee, F., et al. |
| Journal: | Proc. Natl. Acad. Sci. U.S.A. 82 (13), 4360-4364 (1985) |
| GM-CSF | |
| Accession: | M10663 |
| Authors: | Wong, G. G., et al. |
| Journal: | Science 228 (4701), 810-815 (1985) |
| M-CSF | |
| Accession: | M27087 |
| Authors: | Takahashi, M., et al. |
| Journal: | Biochem. Biophys. Res. Commun. 161 (2), 892-901 (1989) |
| M-CSF | |
| Accession: | M37435 |
| Authors: | Wong, G. G., et al. |
| Journal: | Science 235 (4795), 1504-1508 (1987) |
| LFA-3 | |
| Accession: | Y00636 |
| Authors: | Wallner, B. P., et al. |
| Journal: | J. Exp. Med. 166 (4), 923-932 (1987) |
| ICAM-3 | |
| Accession: | X69819 |
| Authors: | de Fougerolles, A. R., et al. |
| Journal: | Unpublished |
| ICAM-2 | |
| Accession: | X15606 |
| Authors: | Staunton, D. E., et al. |
| Journal: | Nature 339 (6219), 61-64 (1989) |
| ICAM-1 | |
| Accession: | J03132 |
| Authors: | Staunton, D. E., et al. |
| Journal: | Cell 52 (6), 925-933 (1988) |
| PECAM | |
| Accession: | M28526 |
| Authors: | Newman, P. J., et al. |
| Journal: | Science 247, 1219-1222 (1990) |
| p150.95 | |
| Accession: | Y00093 |
| Authors: | Corbi, A. L., et al. |
| Journal: | EMBO J. 6 (13), 4023-4028 (1987) |
| Mac-1 | |
| Accession: | J03925 |
| Authors: | Corbi, A. L., et al. |
| Journal: | J. Biol. Chem. 263 (25), 12403-12411 (1988) |
| LFA-1 | |
| Accession.. | Y00796 |
| Authors: | Larson. R., et al. |
| Journal: | J. Cell Biol. 108 (2), 703-712 (1989) |
| CD34 | |
| Accession: | M81104 |
| Authors: | Simmons, D. L., et al. |
| Journal: | J. Immunol. 148, 267-271 (1992) |
| RANTES | |
| Accession: | M21121 |
| Authors: | Schall, T. J., et al. |
| Journal: | J. Immunol. 141, 1018-1025 (1988) |

TABLE 1-continued

| | |
|---|---|
| IL-8 | |
| Accession: | M28130 |
| Authors: | Mukaida, N., et al. |
| Journal: | j. IMMUNOL. 143 (4), 1366-1371 (1989) |
| MIP-1α | |
| Accession: | U72395 |
| Authors: | Fridell, R. A., et al. |
| Journal: | J. Cell. Sci. 110 (Pt 11), 1325-1331 (1997) |
| E-selecton | |
| Accession: | M24736 |
| Authors: | Bevilacqua, M. P., et al. |
| Journal: | Science 243 (4895), 1160-1165 (1989) |
| CD2 | |
| Accession: | M14362 |
| Authors: | Sewell, W. A., et al. |
| Journal-1: | Proc. Natl. Acad. Sci. U.S.A. 83, 8718-8722 (1986) |
| Journal-2: | Proc. Natl. Acad. Sci. U.S.A. 84, 7256-7256 (1987) |
| CD2 | |
| Accession: | M16336 |
| Authors: | Sayre, P. H., et al. |
| Journal: | Proc. Natl. Acad. Sci. U.S.A. 84 (9), 2941-2945 (1987) |
| MCP-1 | |
| Accession: | S69738 |
| Authors: | Li, Y. S., et al. |
| Journal: | Mol. Cell. Biochem. 126 (1), 61-68 (1993) |
| MCP-1 | |
| Accession: | S71513 |
| Authors: | Yoshimura, T., et al. |
| Journal: | Adv. Exp. Med. Biol. 305, 47-56 (1991) |
| L-selection | |
| Accession: | X16150 |
| Authors: | Tedder, T. F., et al. |
| Journal: | J. Exp. Med. 170 (1), 123-133 (1989) |
| P-selection | |
| Accession: | M25322 |
| Authors: | Johnston, G. I., et al. |
| Journal: | Cell 56, 1033-1044 (1989) |
| FLT | |
| Accession: | X94263 |
| Authors: | Mandriota, S. J., et al. |
| Journal: | J. Biol. Chem. 271 (19), 11500-11505 (1996) |
| FLT | |
| Accession: | X51602 |
| Authors-1: | Shibuya, M. et. al. |
| Journal-1: | Oncogene 5 (4), 519-524 (1990) |
| Authors-2: | Han, H. J., et al. |
| Journal-2: | Hum. Mol. Genet. 2 (12), 2204 (1993) |
| Apo-1 | |
| Accession: | X63717 |
| Authors: | Oehm et al., |
| Journal: | J. Biol. Chem., 1992, 267 (15), 10709-15 |
| Fas | |
| Accession: | M67454 |
| Authors: | Itoh et al., |
| Journal: | Cell, 1991, 66 (2), 233-43 |
| TNFR-1 | |
| Accession: | M67454 |
| Authors: | Nophar et al., |
| Journal: | EMBO J., 1990, 9 (10), 3269-78 |
| p55 | |
| Accession: | M58286 |
| Authors: | Loetscher et al., |
| Journal: | Cell, 1990, 61, 351-359 |

TABLE 1-continued

| | |
|---|---|
| WSL-1 | |
| Accession: | Y09392 |
| Authors: | Kitson et al., |
| Journal: | Nature, 1996, 384 (6607), 372-5 |
| DR3 | |
| Accession: | U72763 |
| Authors: | Chinnaiyan et al., |
| Journal: | Science, 1996, 274 (5829), 990-2 |
| TRAMP | |
| Accession: | U75381 |
| Authors: | Bodmer et al., |
| Journal: | Immunity, 1997, 6 (1), 79-88 |
| Apo-3 | |
| Accession: | U74611 |
| Authors: | Marsters et al., |
| Journal: | Curr. Biol., 1996, 6 (12), 1669-76 ; |
| AIR | |
| Accession: | U78029 |
| Authors: | Degli-Esposti et al., |
| Journal: | |
| LARD | |
| Accession: | U94512 |
| Authors: | Screaton et al., |
| Journal: | Proc. Natl. Acad. Sci. USA, 1997, 94 (9), 4615-19 |
| NGRF | |
| Accession: | M14764 |
| Authors: | Johnson et al., |
| Journal: | Cell, 1986, 47 (4), 545-554 |
| DR4 (TRAIL) | |
| Accession: | U90875 |
| Authors: | Pan et al., |
| Journal: | Science, 1997, 276 (5309), 111-113 |
| DR5 | |
| Accession: | AF012535 |
| Authors: | Sheridan et al., |
| Journal: | Science, 1997, 277 (5327), 818-821 |
| KILLER | |
| Accession: | |
| Authors: | Wu et al., |
| Journal: | Nature Genetics, in press, ; |
| TRAIL-R2 | |
| Accession: | AF020501 |
| Authors: | MacFarlane et al., |
| Journal: | J. Biol. Chem., 1997, in press |
| TRICK2 | |
| Accession: | AF018657 |
| Authors: | Screaton et al., |
| Journal: | Curr. Biol., 1997, in press |
| DR6 | |
| Accession: | AF068868 |
| Authors: | Pan et al., |
| Journal: | |
| ICE | |
| Accession: | U13698 |
| Author: | Alnemri, E. S., et al. |
| Journal: | J. Biol. Chem. 270 (9), 4312-4317 (1995) |
| ICE | |
| Accession: | U13697 |
| Author: | Alnemri, E. S., et al. |
| Journal: | J. Biol. Chem. 270 (9), 4312-4317 (1995) |
| ICE | |
| Accession: | U13699 |
| Author: | Alnemri, E. S., et al. |
| Journal: | J. Biol. Chem. 270 (9), 4312-4317 (1995) |

TABLE 1-continued

| VLA-1 | |
|---|---|
| Accession: | X17033 |
| Author: | Takada., et al. |
| Journal: | J. Biol. Chem. 109 (1), 397-407 (1989) |
| CD86 (B7.2) | |
| Accession: | U04343 |
| Author: | Azuma, et al. |
| Journal: | Nature. 366 (6450),76 (1993) |

TABLE 2

| | |
|---|---|
| Picornavirus Family | |
| Genera: | Rhinoviruses: (Medical) responsible for ~50% cases of the common cold.<br>Etheroviruses: (Medical) includes polioviruses, coxsackieviruses, echoviruses, and human enteroviruses such as hepatitis A virus.<br>Apthoviruses: (Veterinary) these are the foot and mouth disease viruses. |
| Target antigens: | VP1, VP2, VP3, VP4, VPG |
| Calcivirus Family | |
| Genera: | Norwalk Group of Viruses: (Medical) these viruses are an important causative agent of epidemic gastroenteritis. |
| Togavirus Family | |
| Genera: | Alphaviruses: (Medical and Veterinary) examples include Senilis viruses, RossRiver virus and Eastern & Western Equine encephalitis.<br>Reovirus: (Medical) Rubella virus. |
| Flariviridue Family | |
| | Examples include: (Medical) dengue, yellow fever, Japanese encephalitis, St. Louis encephalitis and tick borne encephalitis viruses. |
| Hepatitis C Virus: (Medical) these viruses are not placed in a family yet but are believed to be either a togavirus or a flavivirus. Most similarity is with togavirus family. | |
| Coronavirus Family: (Medical and Veterinary) | |
| | Infectious bronchitis virus (poultry)<br>Porcine transmissible gastroenteric virus (pig)<br>Porcine hemagglutinating encephalomyelitis virus (pig)<br>Feline infectious peritonitis virus (cats)<br>Feline enteric coronavirus (cat)<br>Canine coronavirus (dog)<br>The human respiratory coronaviruses cause ~40 cases of common cold. EX. 224E, 0C43<br>Note - coronaviruses may cause non-A, B or C hepatitis |
| Target antigens: | E1 - also called M or matrix protein<br>E2 - also called S or Spike protein<br>E3 - also called HE or hemagglutin-elterose glycoprotein (not present in all coronaviruses)<br>N - nucleocapsid |
| Rhabdovirus Family | |
| Genera: | Vesiliovirus<br>Lyssavirus: (medical and veterinary) rabies |
| Target antigen: | G protein<br>N protein |
| Filoviridue Family: (Medical) | |
| | Hemorrhagic fever viruses such as Marburg and Ebola virus |

TABLE 2-continued

| | |
|---|---|
| Paramyxovirus Family: | |
| Genera: | Paramyxovirus: (Medical and Veterinary)<br>Mumps virus, New Castle disease virus (important pathogen in chickens)<br>Morbillivirus: (Medical and Veterinary)<br>Measles, canine distemper<br>Pneuminvirus: (Medical and Veterinary)<br>Respiratory syncytial virus |
| Orthomyxovirus Family (Medical) | |
| | The Influenza virus |
| Bungavirus Family | |
| Genera: | Bungavirus: (Medical) California encephalitis, LA Crosse<br>Phlebovirus: (Medical) Rift Valley Fever<br>Hantavirus: Puremala is a hemahagin fever virus<br>Nairvirus (Veterinary) Nairobi sheep disease<br>Also many unassigned bungaviruses |
| Arenavirus Family (Medical) | |
| | LCM, Lassa fever virus |
| Reovirus Family | |
| Genera: | Reovirus: a possible human pathogen<br>Rotavirus: acute gastroenteritis in children<br>Orbiviruses: (Medical and Veterinary)<br>Colorado Tick fever, Lebombo (humans)<br>equine encephalosis, blue tongue |
| Retrovirus Family | |
| Sub-Family: | Oncorivirinal: (Veterinary) (Medical) feline leukemia virus, HTLVI and HTLVII<br>Lentivirinal: (Medical and Veterinary) HIV, feline immunodeficiency virus, equine infections, anemia virus Spumavirinal |
| Papovavirus Family | |
| Sub-Family: | Polyomaviruses: (Medical) BKU and JCU viruses |
| Sub-Family: | Papillomavirus: (Medical) many viral types associated with cancers or malignant progression of papilloma |
| Adenovirus (Medical) | |
| | EX AD7, ARD., O. B. - cause respiratory disease - some adenoviruses such as 275 cause enteritis |
| Parvovirus Family (Veterinary) | |
| | Feline parvovirus: causes feline enteritis<br>Feline panleucopeniavirus<br>Canine parvovirus<br>Porcine parvovirus |
| Herpesvirus Family | |
| Sub-Family: | alphaherpesviridue |
| Genera: | Simplexvirus (Medical)<br>HSVI, HSVII<br>Varicellovirus: (Medical - Veterinary)<br>pseudorabies - *varicella zoster* |
| Sub-Family: | betaherpesviridue |
| Genera: | Cytomegalovirus (Medical)<br>HCMV<br>Muromegalovirus |
| Sub-Family: | Gainmaherpesviridue |
| Genera: | Lymphocryptovirus (Medical)<br>EBV - (Burkitts lympho)<br>Rhadinovirus |

TABLE 2-continued

| Poxvirus Family | |
|---|---|
| Sub-Family: | Chordopoxviridue (Medical - Veterinary) |
| Genera: | Variola (Smallpox) |
| | Vaccinia (Cowpox) |
| | Parapoxivirus - Veterinary |
| | Auipoxvirus - Veterinary |
| | Capripoxvirus |
| | Leporipoxvirus |
| | Suipoxvirus |
| Sub-Family: | Entemopoxviridue |
| | Hepadnavirus Family |
| | Hepatitis B virus |
| | Unclassified |
| | Hepatitis delta virus |

| Bacterial pathogens |
|---|
| Pathogenic gram-positive cocci include: pneumococcal; staphylococcal; and streptococcal. Pathogenic gram-negative cocci include: meningococcal; and gonococcal. |
| Pathogenic enteric gram-negative bacilli include: *enterobacteriaceae*; *pseudomonas*, acinetobacteria and *eikenella*; melioidosis; *salmonella*; shigellosis; hemophilus; chancroid; brucellosis; tularemia; *yersinia* (*pasteurella*); *streptobacillus moniliformis* and *spirillum*; *listeria monocytogenes*; *erysipelothrix rhusiopathiae*; diphtheria; cholera; anthrax; donovanosis (granuloma inguinale); and bartonellosis. |
| Pathogenic anaerobic bacteria include: tetanus; botulism; other clostridia; tuberculosis; leprosy; and other mycobacteria. |
| Pathogenic spirochetal diseases include: syphilis; treponematoses: yaws, pinta and endemic syphilis; and leptospirosis. |
| Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. |
| Rickettsial infections include rickettsial and rickettsioses. |
| Examples of mycoplasma and chlamydial infections include: *mycoplasma pneumoniae*; lymphogranuloma venereum; psittacosis; and perinatal chlamydial infections. |
| Pathogenic eukaryotes |
| Pathogenic protozoans and helminths and infections thereby include: amebiasis; malaria; leishmaniasis; trypanosomiasis; toxoplasmosis; *pneumocystis carinii*; babesiosis; giardiasis; trichinosis; filariasis; schistosomiasis; nematodes; trematodes or flukes; and cestode (tapeworm) infections. |

TABLE 4

Production levels of IL-2, IL-10 and IFN-γ of splenocytes after in vitro gD stimulation[a]

| Immunization group | IL-2 (pg/ml) | IFN-γ (pg/ml) | IL-10 (pg/ml) |
|---|---|---|---|
| Naive | 16.7 ± .0.8 | 10.5 ± 0.7 | 17.1 ± 6.12 |
| pgD + pCDNA3 | 134.7 ± 3.5 | 22.4 ± 2.4 | 57.1 ± 4.4 |
| pgD + IL-8 | 756.4 ± 5.4 | 138.5 ± 4.7 | 128 ± 13 |
| pgD + IP-10 | 143.5 ± 3.9 | 31.5 ± 2.5 | 69.9 ± 1.9 |
| pgD + RANTES | 59.9 ± 1.1 | 520 ± 13 | 360 ± 46.5 |
| pgD + MCP-1 | 93.6 ± 4.7 | 17.9 ± 0.5 | 49.7 ± 2.3 |
| pgD + MIP-1α | 345.4 ± 18 | 55.4 ± 1.8 | 22 ± 2.1 |
| pgD + TNF-α | 403 ± 13.3 | 77 ± 6.3 | 86.8 ± 6.2 |
| pgD + TNF-β | 288 ± 5.6 | 20.8 ± 1.5 | 78.3 ± 3.6 |

[a]Each group of Balb/c mice (n = 2) was immunized with gD DNA vaccines (60 μg per mouse) plus chemokine genes (40 μg per mouse) or TNF cDNAs (40 μg per mouse) at 0 and 2 weeks. Two weeks after the last DNA injection, two mice were sacrificed and spleen cells were pooled. A 1 ml aliquot containing $6 \times 10^6$ splenocytes was added to wells of 24 well plates. Then, 1 μg of HSV-2 gD protein/ml was added to each well. After 2 days incubation at 37° C. in 5% $CO_2$, cell supernatants were secured and then used for detecting levels of IL-2, IL-10, and IFN-γ using commercial cytokine kits (Biosource, Intl., Camarillo, Ca.) by adding the extracellular fluids to the cytokine-specific ELISA plates. Samples were assayed in triplicate and the values represent means of released cytokine concentrations ± standard deviation. This represents one of three separate experiments showing the expected result.

TABLE 5

Production levels of MCP-1, MIP-1α, and RANTES of splenocytes after in vitro gD stimulation[a]

| Immunization group | MCP-1 (pg/ml) | MIP-1α (pg/ml) | RANTES (pg/ml) |
|---|---|---|---|
| Naive | 153.8 ± 5.7 | 247 ± 11 | 769 ± 7 |
| pgD + pCDNA3 | 234 ± 5.3 | 747 ± 39 | 817 ± 55 |
| pgD + IL-8 | 322 ± 24 | 1,411 ± 113 | 1,284 ± 53 |
| pgD + IP-10 | 246.3 ± 2.7 | 1,407 ± 459 | 831 ± 52 |
| pgD + RANTES | 189.7 ± 0 | 2,267 ± 219 | 1,077 ± 32 |
| pgD + MCP-1 | 209.2 ± 6.4 | 725 ± 501 | 646 ± 45 |
| pgD + MIP-1α | 142.7 ± 3.3 | 787 ± 94 | 690 ± 39 |

[a]Each group of Balb/c mice (n = 2) was immunized with gD DNA vaccines (60 μg per mouse) plus chemokine genes (40 μg per mouse) at 0 and 2 weeks. Two weeks after the last DNA injection, two mice were sacrificed and spleen cells were pooled. A 1 ml aliquot containing $6 \times 10^6$ splenocytes was added to wells of 24 well plates. Then, 1 μg of HSV-2 gD protein/ml was added to each well. After 2 days incubation at 37° C. in 5% $CO_2$, cell supernatants were secured and then used for detecting levels of RANTES, MCP-1 and MIP-1α using commercial chemokine kits (R&D Systems, Minneapolis, Md.) by adding the extracellular fluids to the cytokine or chemokine-specific ELISA plates. Samples were assayed in triplicate and the values represent means of released chemokine concentrations ± standard deviation. This represents one of three separate experiments showing the expected result.

The invention claimed is:

1. A pyrogen-free composition comprising a plasmid comprising a nucleotide sequence that encodes an immunogen operably linked to regulatory elements and a nucleotide sequence that encodes an immunomodulating protein operably linked to regulatory elements, wherein said immunomodulating protein is DR5, and wherein said immunogen is a pathogen antigen selected from the group consisting of an influenza antigen, an HIV-1 antigen and an HSV antigen.

2. An injectable pharmaceutical composition comprising the pyrogen free composition of claim 1.

3. The pyrogen-free composition of claim 1 wherein said immunogen is an influenza antigen.

4. An injectable pharmaceutical composition comprising the composition of claim 3.

5. The pyrogen-free composition of claim 1 wherein said immunogen is an HIV-1 antigen.

6. An injectable pharmaceutical composition comprising the composition of claim 5.

7. The pyrogen-free composition of claim 1 wherein said immunogen is an HSV antigen.

8. An injectable pharmaceutical composition comprising the composition of claim 7.

9. A method of inducing cytotoxic T cell response in an individual against an immunogen comprising administering by intramuscular injection to said individual a composition comprising a plasmid comprising a nucleotide sequence that encodes an immunogen operably linked to regulatory elements and a nucleotide sequence that encodes an immunomodulating protein operably linked to regulatory elements, wherein said immunomodulating protein DR5, and wherein said immunogen is a pathogen antigen.

10. The method of claim 9 wherein said composition is pyrogen free.

11. The method of claim 9 wherein said immunogen is a viral antigen.

12. The method of claim 11 wherein said composition is pyrogen free.

13. The method of claim 9 wherein the immunogen is selected from the group consisting of: an influenza antigen, an HIV-1 antigen and an HSV antigen.

14. The method of claim 13 wherein said composition is pyrogen free.

15. The method of claim 9 wherein said immunogen is an influenza antigen.

16. The method of claim 15 wherein said composition is pyrogen free.

17. The method of claim 7 wherein said immunogen is an HIV-1 antigen.

18. The method of claim 17 wherein said composition is pyrogen free.

19. The method of claim 9 wherein said immunogen is a HSV antigen.

20. The method of claim 19 wherein said composition is pyrogen free.

21. A pyrogen-free composition comprising two plasmids: a first plasmid comprising a nucleotide sequence that encodes an immunogen operably linked to regulatory elements; and a second plasmid comprising a nucleotide sequence that encodes an immunomodulating protein operably linked to regulatory elements, wherein said immunomodulating protein is DR5, and wherein said immunogen is a pathogen antigen selected from the group consisting of an influenza antigen, an HIV-1 antigen and an HSV antigen.

22. An injectable pharmaceutical composition comprising the pyrogen free composition of claim 21.

23. The pyrogen-free composition of claim 21 wherein said immunogen is an influenza antigen.

24. An injectable pharmaceutical composition comprising the composition of claim 23.

25. The pyrogen-free composition of claim 21 wherein said immunogen is an HIV-1 antigen.

26. An injectable pharmaceutical composition comprising the composition of claim 25.

27. The pyrogen-free composition of claim 21 wherein said immunogen is an HSV antigen.

28. An injectable pharmaceutical composition comprising the composition of claim 27.

29. A method of inducing cytotoxic T cell response in an individual against an immunogen comprising administering to said individual by intramuscular injection a composition comprising two plasmids: a first plasmid comprising a nucleotide sequence that encodes said immunogen operable linked to regulatory elements; and a second plasmid comprising a nucleotide sequence that encodes an immunomodulating protein operably linked to regulatory elements, wherein said immunomodulating protein is DR5, and wherein the immunogen is a pathogen antigen.

30. The method of claim 29 wherein said composition is pyrogen free.

31. A method of claim 29 wherein said immunogen is a viral antigen.

32. The method of claim 31 wherein said composition is pyrogen free.

33. The method of claim 29 wherein the immunogen is selected from the group consisting of: an influenza antigen, an HIV-1 antigen and an HSV antigen.

34. The method of claim 33 wherein said composition is pyrogen free.

35. The method of claim 29 wherein said immunogen is an influenza antigen.

36. The method of claim 35 wherein said composition is pyrogen free.

37. The method of claim 29 wherein said immunogen is an HIV-1 antigen.

38. The method of claim 37 wherein said composition is pyrogen free.

39. The method of claim 29 wherein said immunogen is a HSV antigen.

40. The method of claim 39 wherein said composition is pyrogen free.

* * * * *